(12) United States Patent
Groom et al.

(10) Patent No.: US 11,992,576 B2
(45) Date of Patent: May 28, 2024

(54) EMBOLIC COMPOSITIONS AND METHODS

(71) Applicant: Arsenal Medical, Inc., Watertown, MA (US)

(72) Inventors: Jeffrey Groom, Belmont, MA (US); Craig Wiltsey, Waltham, MA (US); Quynh Pham, Methuen, MA (US); Nikhita Mansukhani, Allston, MA (US); Courtney Guertin, Watertown, MA (US); Lee Core, Needham, MA (US); Upma Sharma, Somerville, MA (US)

(73) Assignee: Arsenal Medical, Inc., Watertown, MA (US)

( * ) Notice: Subject to any disclaimer, the term of this patent is extended or adjusted under 35 U.S.C. 154(b) by 0 days.

(21) Appl. No.: 17/342,945

(22) Filed: Jun. 9, 2021

(65) Prior Publication Data

US 2021/0379207 A1    Dec. 9, 2021

Related U.S. Application Data

(60) Provisional application No. 63/036,564, filed on Jun. 9, 2020.

(51) Int. Cl.

| | |
|---|---|
| *A61K 47/02* | (2006.01) |
| *A61K 47/34* | (2017.01) |
| *A61K 49/04* | (2006.01) |
| *A61L 24/00* | (2006.01) |
| *A61L 24/02* | (2006.01) |
| *A61L 24/04* | (2006.01) |
| *A61L 24/06* | (2006.01) |
| *C08L 83/04* | (2006.01) |

(52) U.S. Cl.
CPC .............. *A61L 24/06* (2013.01); *A61K 47/02* (2013.01); *A61K 47/34* (2013.01); *A61K 49/04* (2013.01); *A61K 49/0409* (2013.01); *A61L 24/0021* (2013.01); *A61L 24/02* (2013.01); *A61L 24/043* (2013.01); *A61L 24/046* (2013.01); *C08L 83/04* (2013.01); *A61L 2400/06* (2013.01); *A61L 2430/36* (2013.01)

(58) Field of Classification Search
None
See application file for complete search history.

(56) References Cited

U.S. PATENT DOCUMENTS

| | | | |
|---|---|---|---|
| 6,251,135 B1 * | 6/2001 | Stinson | A61F 2/82 623/1.34 |
| 2011/0052524 A1 | 3/2011 | de Vries et al. | |
| 2020/0268932 A1 | 8/2020 | Wiltsey et al. | |
| 2021/0085825 A1 | 3/2021 | Wiltsey et al. | |
| 2021/0379239 A1 * | 12/2021 | Groom | A61L 24/02 |

FOREIGN PATENT DOCUMENTS

| | | | | |
|---|---|---|---|---|
| WO | WO-2018081837 A2 * | 5/2018 | ....... | A61B 17/12186 |
| WO | 2020172665 A1 | 8/2020 | | |

OTHER PUBLICATIONS

Sabareesh et al., "Histopathological changes in brain arteriovenous malformations after embolization using Onyx or N-butyl cyanoacrylate", Journal of Neurosurgery, 111(1): p. 105-113, 2009. Abstract.
Siskin et al., "Pathologic Evaluation of a Spherical Polyvinyl Alcohol Embolic Agent in a Porcine Renal Model", Journal of Vascular and Interventional Radiology, 14(1): p. 89-98, 2003. Abstract.
International Search Report and Written Opinion for International application No. PCT/US2021/036636, mailed on Sep. 28, 2021, 14 pages.

\* cited by examiner

*Primary Examiner* — Jake M Vu
(74) *Attorney, Agent, or Firm* — Goodwin Procter LLP

(57) ABSTRACT

The present disclosure pertains to crosslinkable compositions and systems as well as methods for forming crosslinked compositions in situ, including the use of the same for embolizing vasculature including the neurovasculature within a patient, among many other uses.

29 Claims, 14 Drawing Sheets

THE DPE INITIALLY SHEAR THINS AND FLOWS DOWNSTREAM AS A CONTINUOUS STREAM; UPON ENCOUNTERING HIGHER SHEAR, IT BREAKS INTO DISCRETE VOLUMES THAT SHEAR THINS FURTHER TO PENETRATE INTO DISTAL BRANCHES

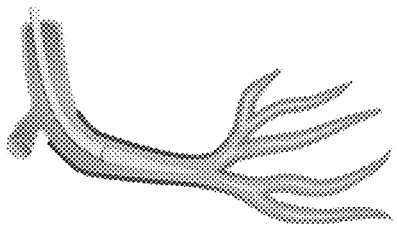

FIG. 1A

AS DISTAL BRANCHES ARE OCCLUDED, FLOW DECREASES PROXIMALLY; IN RESPONSE, THE DPE BEGINS TO INCREASE IN VISCOSITY

FIG. 1B

AS THE VASCULATURE BECOMES MORE OCCLUDED, THE DPE EXITS THE CATHETER AS A VISCOUS PASTE ALLOWING CONTROLLED INJECTION

FIG. 1C

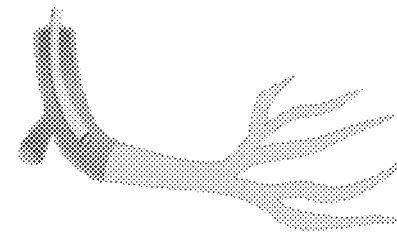

THE RESULT IS COMPLETE CASTING AND OCCLUSION OF THE TARGET VASCULATURE WITHOUT NON-TARGET EMBOLIZATION

FIG. 1D

STRUCTURED FLUID (PASTE AT REST) 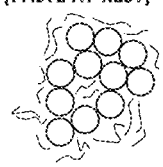 APPLICATION OF SHEAR ➡ LOW VISCOSITY (FLOWABLE) 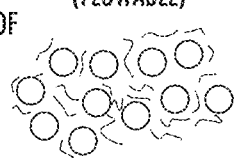 REMOVAL OF SHEAR ➡ STRUCTURED FLUID (PASTE AT REST) 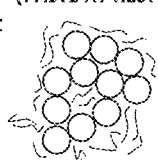 CURE ⇨ ELASTOMER (SOLID) 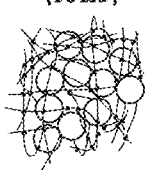

FIG. 2A

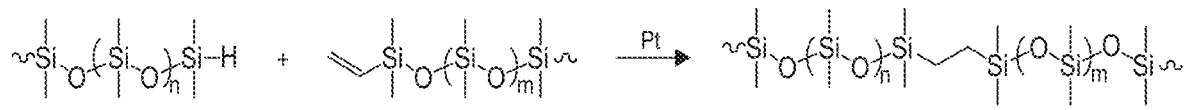

FIG. 2B

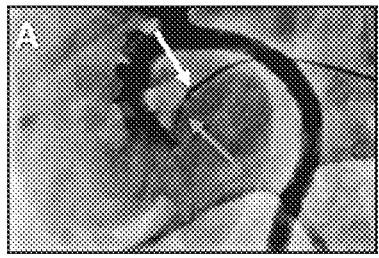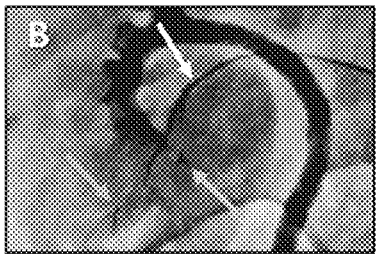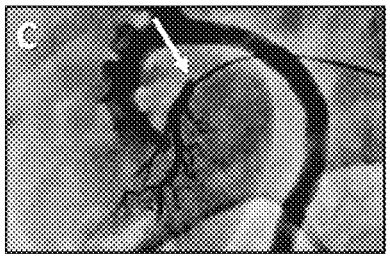
FIG. 3A  FIG. 3B  FIG. 3C
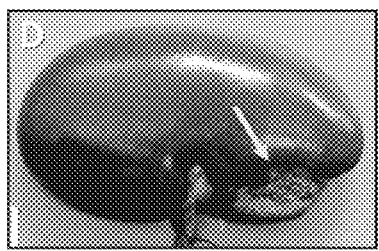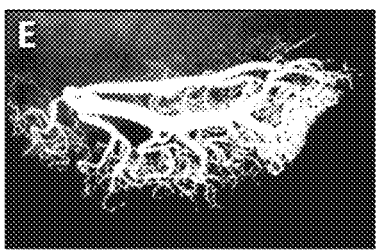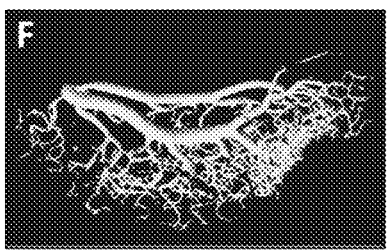
FIG. 3D  FIG. 3E  FIG. 3F
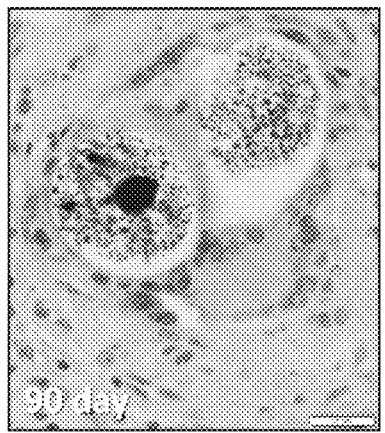
FIG. 4A  FIG. 4B

EMBOLIC COMPOSITIONS AND METHODS

CROSS REFERENCE TO RELATED APPLICATIONS

This application claims the benefit of priority of U.S. Provisional Application No. 63/036,564, filed Jun. 9, 2020, which is incorporated herein in its entirety.

FIELD OF THE DISCLOSURE

The present disclosure pertains to biocompatible crosslinkable compositions, to systems for forming crosslinkable compositions and to methods of using such crosslinkable compositions.

BACKGROUND

Crosslinkable compositions that are capable of forming crosslinked compositions in situ have a number of biomedical advantages including, without limitation the ability to deliver in-situ-forming crosslinked compositions to closed cavities, for example intravascularly, the ability, to deliver in-situ-forming crosslinked compositions to difficult-to-access body sites, the ability of in-situ-forming crosslinked compositions to fill empty space, potential space, or fill space filled with blood, the ability of in-situ-forming crosslinked compositions to support surrounding tissues, and so forth.

SUMMARY

The present disclosure pertains to crosslinkable compositions and kits as well as methods for forming crosslinked compositions in situ.

In one aspect of the disclosure, there is provided a kit comprising (a) a first fluid composition that comprises a first polysiloxane having two or more unsaturated groups, a first silica filler, and/or a first imaging agent, (b) a second fluid composition that comprises a first hydride material having two or more hydride groups, a second silica filler, and/or a second imaging agent and (c) one or more components for mixing and delivery of the first fluid composition and the second fluid composition, wherein at least one of said first and second fluid compositions comprises a catalyst for catalyzing a reaction between the unsaturated groups and the hydride groups, wherein the first and second silica fillers may be the same or different, wherein the first and second imaging agents may be the same or different, and wherein the first fluid composition and the second fluid composition, when mixed, form a crosslinkable composition. In some embodiments of this aspect, the first fluid composition further comprises a second hydride material having two or more hydride groups, the second fluid composition comprises the catalyst, and the first and second hydride material having two or more hydride groups may be the same or different, while in other embodiments, the second fluid further comprises a second polysiloxane having two or more unsaturated groups, the first fluid composition comprises the catalyst, and the first and second polysiloxane having two or more unsaturated groups are the same or different. In other embodiments of this aspect, the first fluid composition comprises the first silica filler and the second fluid composition comprises the second imaging agent, while in still other embodiments, the first fluid composition comprises the first imaging agent and the second fluid composition comprises the second silica agent. In various embodiments, the composition further comprises a plasticizer. In certain embodiments, the crosslinkable composition comprises from 10 to 50 wt % of the second imaging agent.

In another aspect of the disclosure, there is provided a method comprising (a) annealing a first fluid composition that comprises a first polysiloxane having two or more unsaturated groups, a first silica filler, and/or a first imaging agent to form a first annealed fluid composition, (b) annealing a second fluid composition that comprises a first hydride material having two or more hydride groups, a second silica filler and/or a second imaging agent to form a second annealed fluid composition, (c) mixing the first annealed fluid composition and the second annealed fluid composition to form a crosslinkable composition; wherein at least one of said first and second fluid compositions comprises a catalyst for catalyzing a reaction between the unsaturated groups and the hydride groups, wherein the first and second silica fillers may be the same or different, and wherein the first and second imaging agents may be the same or different; and (d) injecting the crosslinkable composition into a body of a patient whereupon the crosslinkable composition crosslinks in the body. In embodiments of this aspect, the method further comprises identifying a blood vessel that branches into smaller distal vessels and injecting the crosslinkable composition into the blood vessel such that the crosslinkable composition flows into the distal vessels and occludes the distal vessels. In certain embodiments, the crosslinkable composition flows into distal vessels having diameters less than 100 microns. In certain embodiments, the crosslinkable composition is injected into the vasculature or neurovasculature of the patient via an inflatable balloon catheter, wherein the balloon is inflated at a site proximal to the injection site and maintained in place for a period of time following injection of the crosslinkable composition.

Further aspects and embodiments of the present disclosure are described in detail below, with reference to the accompanying drawings.

BRIEF DESCRIPTION OF THE DRAWINGS

FIGS. 1A-1D schematically illustrate the progressive embolization of a portion of the vasculature with a crosslinkable composition in accordance with the present disclosure.

FIG. 2A schematically illustrates the progressive behavior of a crosslinkable composition in accordance with the present disclosure during an embolization procedure.

FIG. 2B is a chemical equation representing curing of a crosslinkable composition in accordance with the present disclosure.

FIGS. 3A-3C are angiograms taken at different times during embolization of kidney vasculature showing filling of the kidney vasculature with a crosslinkable composition in accordance with the present disclosure. The upper arrow in FIGS. 3A-3C shows the catheter tip; the lower arrow in FIG. 3A shows a continuous stream of the crosslinkable composition; the lower right arrow in FIG. 3B shows a discrete volume of the crosslinkable composition and the lower left arrow in FIG. 3B shows a volume of the crosslinkable composition exhibiting distal penetration.

FIG. 3D shows a gross image of a kidney at 90 days after embolization, with the arrow pointing to the embolized region.

FIGS. 3E and 3F illustrate x-ray and 3D micro-CT reconstruction images, respectively, of kidney vasculature filled with crosslinkable composition.

FIGS. 4A and 4B show histopathology results at 30 days (FIG. 4A) and 90 days (FIG. 4B) subsequent to kidney embolization using a crosslinkable composition in accordance with the present disclosure.

DETAILED DESCRIPTION

Figure 5:
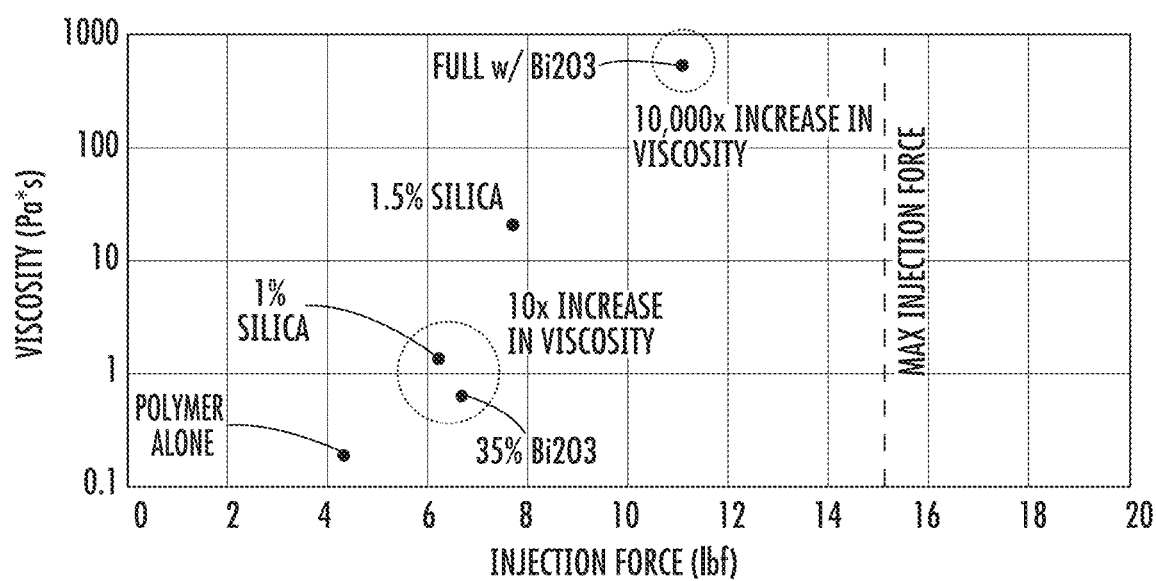
FIG. 5 shows viscosity versus injection force data for various crosslinkable compositions described herein.

As used herein, a material is described as a "fluid" if it is flowable, as is the case with, for example, liquid, semi-solid, paste, gels, suspensions, emulsions and viscoelastic materials.

For the purposes of this disclosure, the term "crosslinkable composition" generally refers to a polymer-based fluid that is capable of being delivered to a delivery site, after which crosslinking (i.e., curing) of the material continues to progress at the delivery site.

In various aspects, the present disclosure pertains to solvent-free crosslinkable compositions that comprise a first polysiloxane having two or more unsaturated groups, a first silica filler, a first imaging agent, a first hydride material having two or more hydride groups, a catalyst for catalyzing a reaction between the unsaturated groups and the hydride groups, an optional second silica filler that is different from the first silica filler, an optional second imaging agent that is different from the first imaging agent, an optional second hydride material having two or more hydride groups that is different from first hydride material having two or more hydride groups, and an optional second polysiloxane having two or more unsaturated groups that is different from the first polysiloxane having two or more unsaturated groups. In various embodiments, the crosslinkable compositions comprise a total amount of at least 10 wt % of the first imaging agent and the optional second imaging agent.

In some aspects, the present invention provides methods in which these biocompatible, crosslinkable compositions are injected into a patient, such as into the vascular system or neurovascular system or a body cavity of a patient.

In various aspects, the present disclosure pertains to kits for forming biocompatible crosslinkable compositions that comprise (a) a first fluid composition comprising a first polysiloxane having two or more unsaturated groups, and optionally a second hydride material having two or more hydride groups. (b) a first dry composition comprising a mixture of a first silica filler and a first imaging agent, or a first silica filler and optionally, a second silica filler, (c) a second fluid composition comprising a first hydride material having two or more hydride groups, and optionally a second polysiloxane having two or more unsaturated groups, (d) an optional second dry composition comprising a first imaging agent or a mixture of a second silica filler and a second imaging agent, and (e) one or more components for mixing and delivery of the first fluid composition, the first dry composition, the second fluid composition and the second dry composition, if present.

In this aspect, at least one of the first and second fluid compositions comprises a catalyst for catalyzing a reaction between the unsaturated groups and the hydride groups, wherein the first and second silica fillers may be the same or different and wherein the first and second imaging agents may be the same or different, and wherein the first fluid composition, the first dry composition, the second fluid composition, and the second dry composition (if present), when mixed, form a crosslinkable composition. In some embodiments, both the first and second fluids comprise the catalyst. In some embodiments, the first fluid composition comprises the catalyst and the second fluid composition does not comprise the catalyst, in which case the second fluid composition may comprise a second polysiloxane having two or more unsaturated groups, which may be the same as or different from the first polysiloxane having two or more unsaturated groups. In some embodiments, the second fluid composition comprises the catalyst and the first fluid composition does not comprise the catalyst, in which case the first fluid composition may comprise a second hydride material having two or more hydride groups that may be the same as or different from the first hydride material having two or more hydride groups. In the case where the first dry composition comprises only the first silica filler, the second dry composition is present and comprises a first imaging agent. The compositions of this aspect of the disclosure, as well as embodiments thereof, are referred to in the Examples as compositions that are "made at the time of injection." In some embodiments, the silica filler is hydrophobic and in other embodiments, the silica filler is hydrophilic. In those embodiments in which a first and second silica filler are included in the composition, one or both silica fillers may be hydrophobic or hydrophilic. In some embodiments, the crosslinkable composition comprises a total amount of at least 10 wt % of the first and second imaging agent (if present).

In embodiments where the kits may include the second dry composition, the first fluid composition and the first dry composition or the second dry composition may be mixed to form a first mixture, and the second fluid composition and the remaining dry composition may form a second mixture, in which case the first mixture and the second mixture may be mixed to form the crosslinkable compositions. Typically, the ratio of the volume of the first mixture to the volume of the second mixture is approximately equal (~1:1), typically ranging, for example, from 4:1 to 1:4, more typically 2:1 to 1:2, among other possible proportions. To enhance mixing, the viscosities of the first and second mixtures may be similar, for example, the oscillatory viscosity of the first and second mixtures at a frequency of 0.1 Hz at 25° C. (see below) may be within +/−60% of In another aspect, the present disclosure pertains to kits for forming crosslinkable compositions that comprise (a) a first fluid composition that comprises a first polysiloxane having two or more unsaturated groups, a first silica filler and/or a first imaging agent, (b) a second fluid composition that comprises a first hydride material having two or more hydride groups, a second silica filler, and/or a second imaging agent, and (c) one or more components for mixing and delivery of the first and second fluid compositions, wherein at least one of the first and second fluid compositions comprises a catalyst for catalyzing a reaction between the unsaturated groups and the hydride groups, wherein the first and second silica fillers may be the same or different, wherein the first and second imaging agents may be the same or different, wherein the first fluid composition and the second fluid composition, when mixed, form a crosslinkable composition. In some embodiments, the crosslinkable composition comprises a total amount of at least 10 wt % of the first and second imaging agents. In some embodiments, both the first and second fluid compositions comprise the catalyst. In some embodiments, the first fluid composition comprises the catalyst and the second fluid composition does not comprise the catalyst, in which case the second fluid composition may comprise a second polysiloxane having two or more unsaturated groups, which may be the same as or different from the first polysiloxane having two or more unsaturated groups. In some embodiments, the second fluid composition comprises the catalyst and the first fluid composition does not comprise the catalyst, in which case the first fluid composition may comprise a second hydride material having two or more hydride groups that may be the same as or different from the first hydride material having two or more hydride groups. In some embodiments, the first fluid composition comprises a silica filler and the second fluid composition comprises an imaging agent, while in other embodiments, the first fluid composition comprises an imaging agent and the second fluid composition comprises a silica filler. In other embodiments, the first and second fluid compositions both comprise silica filler an imaging agent. In some embodiments, at least the first or second silica filler is hydrophobic and in certain embodiments, both the first and second silica fillers are hydrophobic. In other embodiments, both the first and second silica filler are hydrophilic and in other embodiments, at least the first or second silica filler is hydrophilic. Typically, the ratio of the volume of the first fluid composition to the volume of the second fluid composition is approximately equal (~1:1), typically ranging, for example, from 4:1 to 1:4, more typically 2:1 to 1:2, among other possible proportions. To enhance mixing, the viscosities of the first and second fluid compositions may be similar, for example, the oscillatory viscosity of the first and second fluid compositions at a frequency of 0.1 Hz at 25° C. (see below) may be within +/−60% of one another. Compositions of this aspect of the disclosure are referred to in the Examples as "preformulated compositions or "preformulated."

In various aspects, the present disclosure pertains to kits for forming crosslinkable compositions that comprise:

(i) (a) a first fluid composition comprising a first polysiloxane having two or more unsaturated groups and a first silica filler, (b) a second fluid composition that comprises a first hydride material having two or more hydride groups and a second silica filler, (c) a dry composition comprising a first imaging agent, and optionally, a second imaging agent, and (d) one or more components for mixing and delivery of the first fluid composition, the dry composition, and the second fluid composition; wherein the first fluid composition, the dry composition, and the second fluid composition, when mixed, form a crosslinkable composition;

(ii) (a) a first fluid composition comprising a first polysiloxane having two or more unsaturated groups and a first imaging agent, (b) a second fluid composition that comprises a first hydride material having two or more hydride groups and a second imaging agent, (c) a dry composition comprising a first silica filler and optionally a second silica filler, and (d) one or more components for mixing and delivery of the first fluid composition, the second fluid composition, and the dry composition; and wherein the first fluid composition, the dry composition, and the second fluid composition, when mixed, form a crosslinkable composition; or (iii) (a) a first fluid composition comprising a first polysiloxane having two or more unsaturated groups and either a first silica filler and optionally a second silica filler or a first imaging agent and optionally a second imaging agent, (b) a second fluid composition that comprises a first hydride material having two or more hydride groups and either the first silica filler and optionally the second silica filler or the first imaging agent and optionally the second imaging agent, and (c) one or more components for mixing and delivery of the first fluid composition and the second fluid composition, wherein when the first fluid composition comprises the first silica filler and optionally the second silica filler, the second fluid composition comprises the first imaging agent and optionally the second imaging filler, and in the case where the first fluid composition comprises the first imaging agent and optionally the second imaging agent, the second fluid composition comprises the first silica filler and optionally the second silica filler; and wherein the first fluid composition and the second fluid composition, when mixed, form a crosslinkable composition. In each of (i), (ii), and (iii): the first and second silica fillers may be the same or different, the first and second imaging agents may be the same or different, and at least one of the first and second fluid compositions comprises a catalyst for catalyzing a reaction between the unsaturated groups and the hydride groups. Alternatively, each of (i), (ii), and (iii) further comprises a third and/or fourth fluid composition comprising a catalyst for catalyzing a reaction between the unsaturated groups and the hydride groups and a first polysiloxane having two or more unsaturated groups or a first hydride material having two or more hydride groups. In the case where the first fluid composition comprises the catalyst and the second fluid composition does not comprise the catalyst, the second fluid composition may comprise an optional second polysiloxane having two or more unsaturated groups, which may be the same as or different from the first polysiloxane having two or more unsaturated groups. When the second fluid composition comprises the catalyst and the first fluid composition does not comprise the catalyst, then the first fluid composition may comprise an optional second hydride material having two or more hydride groups that may be the same as or different from the first hydride material having two or more hydride groups.

In some embodiments of this aspect of the disclosure, the crosslinkable composition comprises a total amount of at least 10 wt % of the first and second imaging agent (if present). In some embodiments, both the first and second fluid compositions comprise the catalyst. In some embodiments, each of (i), (ii), and (iii) further comprises a third and/or fourth fluid composition comprising a catalyst for catalyzing a reaction between the unsaturated groups and the hydride groups and a first polysiloxane having two or more unsaturated groups or a first hydride material having two or more hydride groups. In some embodiments, at least the first or second silica filler (if present) is hydrophobic and in certain embodiments, both the first and second silica filler (if present) are hydrophobic. In other embodiments, both the first and second silica filler (if present) are hydrophilic and in other embodiments, at least the first or second silica filler (if present) is hydrophilic. Typically, the ratio of the volume of the first fluid composition to the volume of the second fluid composition is approximately equal (~1:1), typically ranging, for example, from 4:1 to 1:4, more typically 2:1 to 1:2, among other possible proportions. To enhance mixing, the viscosities of the first and second fluid compositions may be similar, for example, the oscillatory viscosity of the first and second fluid compositions at a frequency of 0.1 Hz at 25° C. (see below) may be within +/−60% of one another.

In some aspects, any of the above crosslinkable compositions formed by any of the above kits may be injected into a patient using a needle or a catheter.

In various aspects, the present disclosure pertains to methods of forming biocompatible crosslinkable compositions in which a mixture is formed that comprises the following:

(i) a first fluid composition comprising a first polysiloxane having two or more unsaturated groups, (ii) a first dry composition comprising a mixture of a first silica filler and a first imaging agent or a first silica filler and optionally a second silica filler, (iii) a second fluid composition comprising a first hydride material having two or more hydride groups, wherein at least one of the first and second fluid compositions comprises a catalyst for catalyzing a reaction between the unsaturated groups and the hydride groups and (iv) a second dry composition comprising a first imaging agent and optionally a second imaging agent or optionally, a second dry composition comprising mixture of a second silica filler and a second imaging agent. In those embodiments in which the first dry composition comprises the first silica filler and optionally the second silica filler, the second dry composition comprises the first imaging agent and optionally the second imaging agent. In those embodiments in which the first dry composition comprises a mixture of the first silica filler and the first imaging agent, the second dry composition is optional and when present comprises a mixture of the second silica filler and the second imaging agent.

In embodiments of this aspect, the first and second silica fillers may be the same or different, and the first and second imaging agents may be the same or different. In some embodiments, both the first and second fluids comprise the catalyst. In some embodiments, the first fluid composition comprises the catalyst and the second fluid composition does not comprise the catalyst, in which case the second fluid composition may comprise a second polysiloxane having two or more unsaturated groups, which may be the same as or different from the first polysiloxane having two or more unsaturated groups. In some embodiments, the second fluid composition comprises the catalyst and the first fluid composition does not comprise the catalyst, in which case the first fluid composition may comprise a second hydride material having two or more hydride groups that may be the same as or different from the first hydride material having two or more hydride groups. In some embodiments, air bubbles are introduced in the mixture during mixing of the fluid and dry components. In other embodiments, gas may be added during the mixing process to create bubbles in the final mixture. In some embodiments, the bubbles act as the imaging agent.

In embodiments where the methods of forming the crosslinkable compositions comprise forming a mixture that includes the second dry composition, the methods may comprise (a) mixing the first fluid composition and the first dry composition to form a first mixture, (b) mixing the second fluid composition and the second dry composition to form a second mixture, and (c) mixing the first mixture and the second mixture to form the crosslinkable composition. Typically, the ratio of the volume of the first mixture to the volume of the second mixture is approximately equal (~1:1), typically ranging, for example, from 4:1 to 1:4, more typically 2:1 to 1:2, among other possible proportions. To enhance mixing, the viscosities of the first and second mixtures may be similar, for example, the oscillatory viscosity of the first and second mixtures at a frequency of 0.1 Hz at 25° C. may be within +/−60% of one another.

In any of the embodiments of this aspect, the crosslinking composition may be injected into a body of a patient using a needle or catheter whereupon the crosslinkable composition crosslinks in the body.

In various aspects, the present disclosure pertains to methods that comprise (a) forming a crosslinkable composition that comprises a first polysiloxane having two or more unsaturated groups, a first silica filler, a first imaging agent, a first hydride material having two or more hydride groups, a catalyst for catalyzing a reaction between the unsaturated groups and the hydride groups, an optional second silica filler that is different from the first silica filler, an optional second imaging agent that is different from the first imaging agent, an optional second hydride material having two or more hydride groups that is different from first hydride material having two or more hydride groups, and an optional second polysiloxane having two or more unsaturated groups that is different from the first polysiloxane having two or more unsaturated groups. In certain embodiments of this aspect, the method comprises (a) annealing a first fluid composition that comprises a first polysiloxane having two or more unsaturated groups, a first silica filler, and/or a first imaging agent to form a first annealed fluid composition, (b) annealing a second fluid composition that comprises a first hydride material having two or more hydride groups, a second silica filler, and/or a second imaging agent to form a second annealed fluid composition, and (c) mixing the first annealed fluid composition and the second annealed fluid composition to form a crosslinkable composition.

In various embodiments of this aspect of the disclosure, only the first fluid composition or the second fluid composition is annealed prior to mixing of the two fluid compositions. In various embodiments, at least one of the first and second fluid compositions comprises a catalyst for catalyzing a reaction between the unsaturated groups and the hydride groups. In some embodiments, the second fluid composition comprises the catalyst and the first fluid composition does not comprise the catalyst, in which case the first fluid composition may comprise a second hydride material having two or more hydride groups that may be the same as or different from the first hydride material having two or more hydride groups. In embodiments of this aspect, the first and second silica filler (if present) may be the same or different and the first and second imaging agent (if present) may be the same or different. In some embodiments, the first fluid composition comprises silica filler (the first and/or second silica filler) and the second fluid composition comprises imaging agent (the first and/or second imaging agent), while in other embodiments, the first fluid composition comprises the imaging agent (the first and/or second imaging agent) and the second fluid composition comprises the silica filler (the first and/or second silica filler). In other embodiments, the first and second fluid compositions comprise both silica filler(s) and imaging agent(s). In certain embodiments, the crosslinkable composition comprises a total amount of at least 10 wt % of the first imaging agent and second imaging agent. In some embodiments, at least the first or second silica filler is hydrophobic and in certain embodiments, both the first and second silica fillers are hydrophobic. In other embodiments, both the first and second silica filler are hydrophilic and in other embodiments, at least the first or second silica filler is hydrophilic. Typically, the ratio of the volume of the first fluid composition to the volume of the second fluid composition is approximately equal (~1:1), typically ranging, for example, from 4:1 to 1:4, more typically 2:1 to 1:2, among other possible proportions. To enhance mixing, the viscosities of the first and second fluid compositions may be similar, for example, the oscillatory viscosity of the first and second fluid compositions at a frequency of 0.1 Hz at 25° C. (see below) may be within +/−60% of one another.

In those embodiments of this aspect in which the first fluid composition and second fluid composition are separately annealed, the annealing can be carried out in any manner that does not compromise the various components of the fluid compositions. For example, annealing may be carried out by allowing the fluid compositions to rest at room temperature for a sufficient period of time to allow the compositions to reach an equilibrium and/or improve ductility of the compositions. Alternatively, annealing of the compositions may involve heating the fluid compositions for a sufficient period of time such as 4 to 10 days to allow the compositions to reach an equilibrium and/or improve ductility of the compositions, e.g., 50° C. to 80° C., such as 70° C. for 7 days.

In any of the embodiments of this aspect, the crosslinkable composition may be injected into a body of a patient using a needle or catheter whereupon the crosslinkable composition crosslinks in the body.

In various aspects, the present disclosure pertains to methods that comprise (a) forming a crosslinkable composition that comprises:

(i) a first fluid composition comprising a first polysiloxane having two or more unsaturated groups and a first silica filler, a second fluid composition comprising a first hydride material having two or more hydride groups and a second silica, filler, that is the same or different from the first silica filler, a dry composition comprising a first imaging agent and optionally a second imaging agent that is the same or different from the first imaging agent;

(ii) a first fluid composition comprising a first polysiloxane having two or more unsaturated groups and a first imaging agent, a second fluid composition comprising a hydride material having two or more hydride groups and a second imaging agent that is the same or different from the first imaging agent, a dry composition comprising a first silica filler and optionally a second silica filler that is the same or different from the first silica filler; or (iii) a first fluid composition comprising a first polysiloxane having two or more unsaturated groups and either a first silica filler and optionally a second silica filler that is the same or different from the first silica filler or a first imaging agent and optionally a second imaging agent that is the same or different from the first imaging agent, a second fluid composition comprising a first hydride material having two or more hydride groups and either the first silica filler and optionally the second silica filler or the first imaging agent and optionally the second imaging agent, wherein when the first fluid composition comprises the first silica filler and optionally the second silica filler, the second fluid composition comprises the first imaging agent and optionally the second imaging filler, and in the case where the first fluid composition comprises the first imaging agent and optionally the second imaging agent, the second fluid composition comprises the first silica filler and optionally the second silica filler, wherein in each of (i), (ii), and (iii) at least one of the first and second fluid compositions comprises a catalyst for catalyzing a reaction between the unsaturated groups and the hydride groups. Alternatively, each of (i), (ii), and (iii) further comprises a third or fourth fluid compositions comprising a catalyst for catalyzing a reaction between the unsaturated groups and the hydride groups and a first polysiloxane having two or more unsaturated groups or a first hydride material having two or more hydride groups. Upon forming the crosslinkable composition of (i). (ii), or (iii), the composition is injected into a body of a patient whereupon the crosslinkable composition crosslinks in the body. In the case where the first fluid composition comprises the catalyst and the second fluid composition does not comprise the catalyst, the second fluid composition may comprise an optional second polysiloxane having two or more unsaturated groups, which may be the same as or different from the first polysiloxane having two or more unsaturated groups. When the second fluid composition comprises the catalyst and the first fluid composition does not comprise the catalyst, then the first fluid composition may comprise an optional second hydride material having two or more hydride groups that may be the same as or different from the first hydride material having two or more hydride groups.

In various embodiments, the crosslinkable compositions described herein, including the crosslinkable compositions formed by any of the above kits or methods, may have a viscosity as measured by oscillatory rheology at 0.1 Hz and 1% strain at 25° C. that ranges from 100 Pa*s or less to 10,000 Pa*s or more, for example, ranging anywhere from 100 Pa*s to 250 Pa*s to 500 Pa*s to 1000 Pa*s to 2500 Pa*s to 5000 Pa*s to 10000 Pa*s (in other words, ranging between any two of the preceding values).

In various embodiments, the kits described herein, including the cured compositions formed by any of the above kits or methods, may be subjected to terminal sterilization, i.e., sterilization of the composition in its final container. For example, the kits may be exposed to electron-beam (e-beam) irradiation or ethylene oxide gas, dry heat, gamma irradiation, nitric oxide, x-ray irradiation, and the like. In some embodiments, components of the kits would be subjected to terminal sterilization. In other embodiments, components of the kits are sterilized using aseptic filtration rather than terminal sterilization.

In various embodiments, the crosslinkable compositions described herein, including the crosslinkable compositions formed by any of the above kits or methods, may exhibit shear thinning fluid properties. For example, the crosslinkable compositions may have a viscosity as measured by oscillatory rheology at 0.1 Hz and 1% strain at 25° C. that is at least ten-fold, beneficially at least one-hundred-fold, more beneficially at least five-hundred-fold, greater than a viscosity of the composition as measured by flow rheology at a frequency of 30 Hz at 25° C.

In various embodiments, the crosslinkable compositions described herein, including the crosslinkable compositions formed by any of the above kits or methods, may have a gel time at temperatures of 25° C. to 37° C. ranging from 3 minutes or less to 60 minutes or more, for example, ranging anywhere from 3 minutes to 5 minutes to 10 minutes to 15 minutes to 20 minutes to 25 minutes to 30 minutes to 45 minutes to 60 minutes.

Rheological measurements may be made using a TA Instruments (Newcastle, Del., USA) Discovery HR-1 rheometer. For viscosity measurements the crosslinkable composition is placed into a 25 mm parallel plate setup (using sandblasted plates to avoid slip), a Peltier system (TA Instruments) is used to control that temperature and maintain a gap of 1000 microns and (i) a first viscosity is measured using oscillatory rheology defined within the linear region, generally at 1% strain and 0.1 Hz (lower shear) at 25° C. and (ii) a second viscosity is measured using flow rheology at a frequency of 30 Hz at 25° C. (higher shear). The higher shear value provides an indication of the properties of the composition under shear conditions similar to the conditions placed on the composition during delivery from a delivery device. The lower shear value provides an indication of the properties of the composition once implanted within the body where shear conditions are experienced having low strain and low frequency. The preceding measurements are made within three minutes after the crosslinkable composition is formed.

For gel time measurements, the composition is loaded onto a rheometer with a 25 mm parallel plate setup (see above) and measurements are taken at constant frequency and strain (f=10 rad/s, γ=1%) over the course of 90 minutes at 37° C. to observe the cure time and profile; gel time (time of cure) is defined as the time at which a peak of the phase angle (δ) is observed. Curing time will change based on temperature and curing will take place in the within the body at 37° C. at a faster rate than at room temperature (25° C.).

In various embodiments, the crosslinkable compositions described herein, including the crosslinkable compositions formed by any of the above kits or methods, can be injected by hand.

In various embodiments, the crosslinkable compositions described herein may have an injection force ranging from 1 to 30 lbf.

Injection force is an important parameter that determines a formulation's suitability for clinical use. In the present disclosure, injection force is determined by using an Instron setup similar to that described by Chen et al., Chen, M. H., et al., "Methods To Assess Shear-Thinning Hydrogels for Application As Injectable Biomaterials," *ACS biomaterials science & engineering*, 2017, 3(12): pp. 3146-3160. Samples are loaded into 1 mL Merit Medallion syringes and then affixed vertically with the plunger facing up. A 100 cm long catheter with a diameter appropriate for the target indication is then attached to the syringe and the test head of the Instron is advanced at a rate of 25 mm/min (equivalent to 0.5 mL/min injection rate). Injection force measurements are made within 3 minutes after the crosslinkable composition is initially mixed.

In various aspects, the crosslinkable compositions described herein, including the crosslinkable compositions formed by any of the above kits or methods, may be employed in methods whereby the crosslinkable compositions are delivered to a body of a patient, for example, by injecting any of the crosslinkable compositions onto any tissue or into any body cavity or body lumen of a patient using any suitable device.

In certain embodiments, a composition of the disclosure is injected into the vasculature where it initially shear thins and flows downstream as a continuous stream; upon encountering higher shear, it breaks into discrete volumes that shear thins further to penetrate into distal branches (FIG. 1A). As distal branches are occluded, flow decreases proximally; in response, the composition increases in viscosity. (FIG. 1B). As the vasculature becomes more occluded, the composition exits the catheter as a viscous paste allowing controlled injection. (FIG. 1C). The result is complete casting and occlusion of the target vasculature without non-target embolization. (FIG. 1D).

In certain embodiments, the methods comprise injecting the crosslinkable compositions into the vasculature and can be used, for example, for occlusion of the vasculature (e.g., vascular embolization or neurovascular embolization) including portal vein embolization, embolization of tumors, including meningioma tumors, and peripheral tumors, presurgical embolization of tumors to minimize blood loss, chronic subdural hematoma, brain aneurysms, arteriovenous malformations, arteriovenous fistulas, gastrointestinal bleeds, bleeding due to trauma, prostate artery embolization, uterine artery embolization, visceral aneurysms, varicocele, varices, treatment for pelvic congestion, epistaxis. and treatment of endoleaks, among others.

In some embodiments, the crosslinkable compositions described herein, including the crosslinkable compositions formed by any of the above kits or methods, may be introduced into the vasculature at a site proximal to the site to be treated through the use of an occlusion device or occlusion technique. In some embodiments, the injection catheter itself can be used to exclude blood flow. In other embodiments, the occlusion device is a balloon catheter. The shape, location and material of the inflatable balloon are selected such that when inflated, the balloon conforms to the shape of the vasculature, or at least a portion thereof, without appreciably deforming the vessel walls. In this manner the balloon is used to occlude a selected branch of the vasculature such that the composition may be injected deep into the vasculature without vessel constriction or significant reflux of the composition beyond the site of injection, enabling deeper penetration of the composition into the vasculature. In general, the balloon is maintained in place after introduction of the composition into the vasculature until the composition cures. A balloon catheter is particularly useful for injecting compositions that are formed at the time of injection as described above, e.g., those compositions formed by mixing fluid and dry components immediately prior to injecting the crosslinkable composition into a patient.

In some embodiments, the method comprises injecting a composition described herein, including the crosslinkable compositions formed by any of the above kits or methods, into the vasculature of a patient for distal penetration treatment such as portal vein embolization, tumor embolization, and the like.

In some embodiments, the compositions of the disclosure may be injected into the vascular in conjunction with another device such as a coil, plug, or stent graft.

In some embodiments, the method comprises identifying a blood vessel that branches into smaller distal vessels (for example, distally branching into a capillary bed) and injecting the crosslinkable composition into the blood vessel such that the crosslinkable composition flows into the distal vessels and occludes the distal vessels. The crosslinkable composition flows into distal vessels having diameters less than 100 microns, such as from 100 microns to 30 microns in some cases.

For example, the crosslinkable compositions may be injected into the portal vein as part of a portal vein embolization (PVE) procedure. PVE, is a technique used before hepatic resection to increase the size of liver segments that will remain after surgery. This therapy redirects portal blood to segments of the future liver remnant (FLR), resulting in hypertrophy. PVE is indicated when the FLR is either too small to support essential function or marginal in size and associated with a complicated postoperative course.

As another example, the crosslinkable compositions may be injected into the middle meningeal artery (MMA). Many diseases, including dural arteriovenous fistula (DAVF), pseudoaneurysm, true aneurysm, traumatic arteriovenous fistula (AVF), moyamoya disease (MMD), recurrent chronic subdural hematoma (CSDH), migraine and meningioma, can involve the middle meningeal artery and can be treated by administration of a composition of the disclosure into the MMA.

Endovascular MMA embolization is an emerging treatment for chronic subdural hematoma (cSDH), with preliminary data suggesting that this minimally invasive therapy may be more efficacious and equally as safe compared to conventional, more invasive surgery.

As another example, the crosslinkable compositions may be injected into a hypervascular brain tumor, for example a meningioma, prior to surgical resection. This therapy has been shown to reduce operative blood loss and reduce surgical procedure time.

As noted above, in various embodiments, the crosslinkable compositions have shear thinning properties. As seen from the Examples below, the present disclosure describes crosslinkable compositions that are flow-responsive materials that allow for the substantially complete fill and occlusion of targeted vasculature when injected into the targeted vasculature. Without wishing to be bound by theory, it is believed that, at the start of the procedure, flow velocity is high leading to a high shear rate within the blood vessel and its distal branches; thus, when the crosslinkable composition initially exits the catheter, it encounters high shear and becomes a low viscosity fluid that deeply penetrates into distal branches. As occlusion occurs in the distal branches, flow velocity is diminished proximally; in response, the shear decreases and the viscosity of the crosslinkable composition increases. Flow continues to diminish further as the vasculature becomes even more occluded proximally; consequently, the crosslinkable composition returns to a high viscosity resting state, behaving, for example, as a viscous paste. The end result is formation of an entire cast of the vasculature down to distal vessels that induces complete occlusion. This process is illustrated schematically in FIGS. 1A-1D.

In various aspects, the crosslinkable compositions described herein are delivered to a delivery site in a body of a patient through the use of a suitable delivery device or system. In various embodiments, the delivery system may comprise a catheter. As used herein, a "catheter" is any device that may be introduced into or adjacent to a patient's body or target location within a patient's body, and comprises at least one lumen of any appropriate size, shape or configuration for the movement of fluid therethrough. In certain embodiments, a catheter may be employed that ranges from 100-200 cm in length and has a diameter appropriate for the target indication (e.g., from 0.016" to 6 Fr), among many other possibilities. In certain embodiments, the catheter is a balloon catheter. As used herein, crosslinkable compositions described as being "injected," "deposited," "delivered" and the like include crosslinkable compositions that are placed via a delivery system at a delivery location on or within a patient's body using any suitable means, including syringe-based injection. In some embodiments, the crosslinkable compositions are delivered by hand. In other embodiments, depending on fluid viscosity, a hand-powered syringe-assist, pneumatic or mechanical pressure pump, or other device may be used to control the flow rate and/or improve ease/force of injection. As previously noted, the crosslinkable compositions described herein, including the crosslinkable compositions formed by any of the above kits or methods, comprise a first silica filler (and a second silica filler, in some cases). Examples of silica fillers include fumed silica, precipitated silica, and hydrophobic silica, among others.

Silica fillers have been found to impart shear-thinning properties to the crosslinkable compositions of the present disclosure. Such properties allow, for example, for microcatheter injection and flow responsiveness for distal penetration and proximal control when flow is reduced. Such silica fillers have also been found to provide crosslinkable compositions in the form of a structured fluid or paste, which allows a radiopaque agent or other imaging agent to remain suspended, and allows for even radiopacity or imaging during injection.

Without wishing to be bound by theory, it is believed that the particles in the crosslinkable compositions of the present disclosure imparts shear-thinning behavior through the formation of a reversible hydrogen bonded network. For example, in the case where the crosslinkable composition comprises polydimethylsiloxane (PDMS) having two or more unsaturated groups (and in some embodiments comprise PDMS having two or more hydride groups), and with reference to FIG. 2A, silica particles (shown with spheres) interact with each other and with PDMS (shown with lines) to form a high-viscosity structured fluid. When shear force is applied, the silica-silica interactions are disrupted, and the viscosity of the material drops temporarily and reversibly. As soon as the shear force is removed, immediate recovery of silica-silica interactions restores the paste-like structure of the crosslinkable composition. Thus, as a consequence of this property, the material acts as a low viscosity, flowable material when injected through a catheter and continues to be so upon entering a blood vessel, where the flow of blood continues to shear-thin the material and carry it distally to fill and cast distal branches. Over time, the material cures into a permanent elastic solid through hydrosilylation (shown in FIG. 2B); this point is known as the gel time. As vinyl and hydride groups react to form carbon-carbon covalent bonds (shown with dots in FIG. 2A), the polymer network becomes chemically crosslinked.

In various embodiments, the crosslinkable compositions described herein, including the crosslinkable compositions formed by any of the above kits or methods, comprise a total amount of from 0.25 wt % or less to 10 wt % or more of silica filler, for example, ranging from 0.25 wt % to 0.5 wt % to 1 wt % to 2 wt % to 5 wt % to 7.5 wt % to 10 wt %.

In various embodiments, the silica filler in the crosslinkable compositions described herein, including the crosslinkable compositions formed by any of the above kits or methods, is characterized by a surface area of 50 $m^2/g$ or less to 1000 $m^2/g$ or more, for example ranging from 50 $m^2/g$ to 100 $m^2/g$ to 200 $m^2/g$ to 500 $m^2/g$ to 1000 $m^2/g$.

As noted above, in various embodiments, the silica filler in the crosslinkable compositions described herein, including the crosslinkable compositions formed by any of the above kits or methods, is hydrophobic, e.g., has hydrophobic groups chemically bonded to the surface such as by treatment of silica with hexamethyldisilazane (HMDS). The hydrophobic groups may be alkyl or polydimethylsiloxane for example. In those embodiments in which the compositions comprise two different silica fillers, one or both silica fillers may be hydrophobic.

As previously noted, the crosslinkable compositions described herein, including the crosslinkable compositions formed by any of the above kits or methods, comprise a first imaging agent (and the second imaging agent in some embodiments). Such imaging agents impart visibility for imaging (e.g. under fluoroscopy). For example, radiopaque agents impart radiopacity for radiographic imaging (e.g. under fluoroscopy). Radiopaque agents may be selected, for instance, from radiopaque metals, radiopaque metal alloys, radiopaque metal oxides and radiopaque polymers (e.g., iodinated polymers). In some embodiments, a radiopaque agent may be selected from tantalum, tungsten, bismuth (III) oxide, zinc oxide, titanium dioxide and zinc titanate. In some embodiments, imaging agents may include MRI (magnetic resonance imaging) contrast agents, ultrasound contrast agents. Imaging agents for use in conjunction with magnetic resonance imaging (MRI), include agents that contain elements with relatively large magnetic moment such as gadolinium, manganese and iron (e.g., Gd(III), Mn(II), Fe(III), etc.) and compounds (including chelates) containing the same, such as gadolinium ion chelated with diethylenetriaminepentaacetic acid. Nonlimiting examples of imaging agents for use in conjunction with ultrasound imaging include microbubbles filled with suitable gases such as air, carbon dioxide, hydrogen, oxygen, nitrogen, sulfur hexafluoride, perfluorobutane or octafluoropropane, among others.

In various embodiments, the crosslinkable compositions described herein, including the crosslinkable compositions formed by any of the above kits or methods, comprise a total amount of from 1 wt % to 50 wt % or more of imaging agent, for example, ranging from 1 wt % to 5 wt % to 10 wt % to 15 wt % to 20 wt % to 25 wt % to 30 wt % to 35 wt % to 40 wt % to 45 wt % to 50 wt %.

In various embodiments, the imaging agent may be present in a size ranging from 10 nm to 20 µm. For example, the use of nanoparticle size imaging agent can minimize CT artifact allowing for better imaging on follow-up.

In various embodiments, metal oxides are used as a radiopaque agent. Metal oxides such as bismuth oxide (typically bismuth trioxide) can provide shear-thinning advantages.

In addition, bismuth oxide is not flammable (e.g., compared to commonly used tantalum), therefore risk of sparking and fire during surgical resection with electrocautery tools is minimized. Bismuth oxide also provides the crosslinked composition with a bright yellow color which clearly indicates which vessels have been embolized, which can lead, for example, to more accurate surgical resection and reduced complications.

As indicated above, metal oxides such as bismuth oxide can provide shear-thinning advantages. This is particularly apparent when provided in combination with silica. In this regard, as seen from Example 8 below and FIG. 5, mixing dry components (e.g., silica and radiopaque agent) with fluid components (e.g., the remaining components) at the time of injection (instead of storing with the components compounded) maximizes shear thinning of material (reduction in injection force for a given viscosity), with less silica required and little concern of long term stability.

In some embodiments of each of the aspects of the disclosure, particle dispersion may have a significant impact on the material properties of the various composition of the disclosure and can be controlled by various means including, for example, by ensuring sufficient wetting of the dry components of the compositions, high shear dispersion of the particles in the polymers, and other processing steps known to those in the art.

As previously noted, the crosslinkable compositions described herein, including the crosslinkable compositions formed by any of the above kits or methods, comprise a first polysiloxane having two or more unsaturated groups (and a second polysiloxane having two or more unsaturated groups, in some embodiments).

In some embodiments, the crosslinkable compositions described herein comprise a total amount of polysiloxane(s) having two or more unsaturated groups ranging from 20 wt % or less to 60 wt % more, for example ranging from 20 wt % to 25 wt % to 30 wt % to 35 wt % to 40 wt % to 45 wt % to 50 wt % to 55 wt % to 60 wt %.

As used herein, the terms "polysiloxane" and "polysiloxane-based polymer" refer to polymers having repeating —Si—O— bonds in the polymer backbone. Polysiloxanes for use in the present disclosure include those comprising homopolymer and/or copolymer regions consisting of, or containing, one or more organo-siloxane monomers, including dialkylsiloxane monomers, diarylsiloxane monomers and/or alkylarylsiloxane monomers, such as dimethylsiloxane, diethylsiloxane, methylethylsiloxane, methylphenylsiloxane and/or diphenylsiloxane monomers, to name a few examples. In various beneficial embodiments described herein, polydialkylsiloxane-based polymers, including polydimethylsiloxane (PDMS)-based polymers, are employed as polysiloxanes. PDMS-based polymers are beneficial for use in the present disclosure for a variety of reasons, including low relative viscosity at higher molecular weights (MW), their well-established use in medical devices and implants, and their inherent biocompatibility.

For the purposes of this disclosure, "unsaturated groups" are groups with less than the maximum number of hydrogen atoms per carbon (not saturated with hydrogen atoms), including groups with carbon-carbon double or triple bonds such as alkene or alkyne groups. Specific examples of polysiloxanes having two or more unsaturated groups include unsaturated-group-terminated polysiloxanes such as vinyl-terminated PDMS, acrylate-terminated PDMS, or methacrylate-terminated PDMS).

In some embodiments, the unsaturated groups of the polysiloxane(s) are selected from —CH=CH$_2$ and —C≡CH groups, with specific examples including vinyl-terminated polysiloxanes, acrylate-terminated polysiloxanes, methacrylate-terminated polysiloxanes, and alkyne-terminated polysiloxanes.

In some embodiments, the polysiloxane(s) is/are linear.

In some embodiments, the polysiloxane(s) has/have a weight average molecular weight ranging from 250 Da or less to 10000 Da or more, for example ranging from 250 Da to 500 Da to 1000 Da to 2500 Da to 5000 Da to 10000 Da. In some embodiments, polysiloxanes with lower molecular weight (500 Da to 10000 Da) might be blended with a smaller percentage of higher molecular weight polysiloxane (10000 Da to 100000 Da). In some embodiments, the compositions include a mixture of two polysiloxanes having different molecular weights, e.g., any combination of a lower molecular weight (500 to 5000 Da) and a higher molecular weight (5000-10000 Da) polysiloxane. In some embodiments the lower molecular weight polysiloxane is preferentially between 500 to 2100 Da. For example,

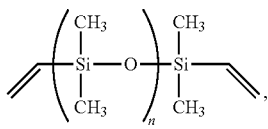

where n is an integer may be used.

As previously noted, the crosslinkable compositions described herein, including the crosslinkable compositions formed by any of the above kits or methods, comprise a first hydride material having two or more hydride groups (and a second hydride material having two or more hydride groups in some embodiments).

For purposes of the present disclosure a "hydride group" is a reactive group in which hydrogen is bonded to another atom and is typically a silicon hydride group in which hydrogen is bonded to a silicon atom. In certain embodiments, hydride materials are employed which contain from 2 to 20 hydride groups per molecule, for example ranging from 2 to 3 to 5 to 7 to 10 to 15 to 20 hydride groups per molecule.

In some embodiments, the crosslinkable compositions described herein comprises a total amount of hydride material(s) having two or more hydride groups ranging from 10 wt % or less to 40 wt % or more, for example, ranging from 10 wt % to 15 wt % to 20 wt % to 25 wt % to 30 wt % to 35 wt % to 40 wt %.

In some embodiments, the hydride material(s) having two or more hydride groups is/are multifunctional polysiloxane hydride(s).

In some embodiments, the multifunctional polysiloxane hydride(s) is/are linear polysiloxane hydride(s). In some of these embodiments, the linear polysiloxane hydride(s) comprise hydride end groups and/or hydride side groups.

In some embodiments, the multifunctional polysiloxane hydride(s) has/have a weight average molecular weight ranging from 250 Da or less to 10000 Da or more, for example ranging from 250 Da to 500 Da to 1000 Da to 2500 Da to 5000 Da to 10000 Da.

Specific examples of hydride material(s) having two or more hydride groups include both small molecule hydrides and polymeric hydrides. Polymeric hydrides include multifunctional polysiloxane hydrides including multifunctional PDMS hydrides, for example,

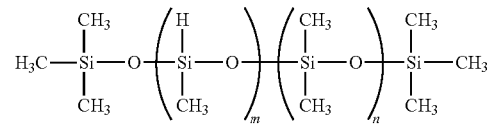

where n and m are integers. Such compounds are also referred to herein as "hydride crosslinker." Examples of multifunctional PDMS hydrides further include hydride-terminated PDMS, for example,

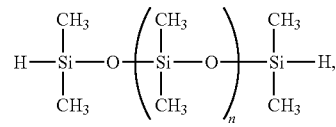

where n is an integer Such compounds are also referred to herein as "linear hydride".

It is further noted that an excess amount of hydride groups (stoichiometrically) relative to vinyl groups can lead to the production of gas. In some embodiments, this gas is used as an imaging agent. In other embodiments, where gas is not desired, the crosslinkable compositions may have a ≥0.9:1 vinyl-group-to-hydride-group molar ratio. In some embodiments, the crosslinkable compositions may have a vinyl-group-to-hydride-group molar ratio ranging from 1.1:1 to 1.5:1, typically ranging from 1.2:1 to 1.4:1.

As seen from the above, polysiloxanes having two or more unsaturated groups for use in the present disclosure can be formed using polydimethylsiloxane (PDMS) elastomers. Similarly, hydride materials having two or more hydride groups for use in the present disclosure can be formed using PDMS elastomers. Such materials have several potential advantages including those to follow. First, PDMS is known to be biocompatible and non-cytotoxic (see also Example 7 below). Moreover, as seen from Example 6 below, being hydrophobic allows for complete casting of vessels, wherein blood is pushed from the blood vessels during embolization. In addition, PDMS cures into a soft elastic rubber, facilitating surgical resection, where necessary. Furthermore, as seen from Example 8 below, PDMS polymers having low molecular weight may be employed to reduce overall injection force. Finally, iodinated PDMS may be used in some embodiments, which could eliminate or decrease the level of imaging particles needed.

As previously noted, the crosslinkable compositions described herein, including the crosslinkable compositions formed by any of the above kits or methods, comprise a catalyst for catalyzing a reaction between unsaturated groups and hydride groups. Examples of such catalysts include for example, a platinum catalyst, a rhodium catalyst, a ruthenium catalyst, a palladium catalyst, an iridium catalyst, a boron trihydride catalyst, and a phosphine catalyst.

As seen from Example 7 below, catalyzed bulk cure allows for more distal penetration and complete casting (remains flowable until cure unlike commercially available liquid embolics which react with the environment).

The crosslinkable compositions described herein, including the crosslinkable compositions formed by any of the above kits or methods, may also optionally contain a catalyst modifier.

The crosslinkable compositions described herein, including the crosslinkable compositions formed by any of the above kits or methods, may also optionally contain one or more physical crosslinking agent comprising a plurality of hydrogen bonding groups.

In various embodiments, physical crosslinking agents for use in the crosslinkable compositions of the present disclosure may comprise a plurality of hydroxy (—OH) groups as hydrogen bonding groups. Examples of physical crosslinking agents include, hydroxy-terminated polymers and dendrimers such as hydroxy-terminated polysiloxanes (e.g., carbinol (hydroxy) terminated polydimethysiloxane), hydroxy-terminated poly(alkylene oxides) including hydroxy-terminated polyethylene oxide and hydroxy-terminated polypropylene oxide, and hydroxy-terminated polyvinyl alcohol. Such hydroxy-terminated polymers may be, for example, linear, or may be multiarmed or dendritic, for example, having three, four, five, six or more arms, one specific example of which is a three-arm polymer of the formula,

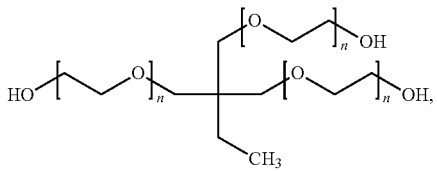

where n is an integer. Other examples include sugars, such as sucrose, cellulose, glucose, and dextrose, and potassium phthalate, polyols (e.g., glycerol, diglycerol, triglycerol, tetraglycerol, pentaglycerol, hexaglycerol, ethylene glycol, propylene glycol, butylene glycol, 1,5-pentane diol, 1,6-hexane diol, trimethylolpropane, 1,2,6-hexane triol, pentaerythritol, sorbitol, mannitol, hydroxypropylmethylcellulose or hydroxypropylethylcellulose) and acrylates (e.g. poly (acrylic acid), 2-hydroxyethylmethacrylate, poly (methyl methacrylate-co-ethyl acrylate)).

In various embodiments, plasticizers may be added to the composition. Plasticizers can be used to improve the ductility of the material. For example, a composition without plasticizer may form rounded or beaded droplets when injected while a composition with plasticizer forms elongated droplets. In some embodiments, the plasticizer may be hydrophilic and in others it may be hydrophobic. In some embodiments, the plasticizer may be used to enhance the cohesion of the composition. Examples of plasticizers include trimethylolpropane ethoxylate (TMPEO), sucrose solution, dimethylsiloxane-(80% ethylene oxide) block copolymer, Dimethylsiloxane-(30-35% ethylene oxide) block copolymer, polydimethylsiloxane, trimethylsiloxy terminated, and oils (including but not limited to coconut oil or sunflower oil).

The crosslinkable compositions described herein, including the crosslinkable compositions formed by any of the above kits or methods, may also optionally contain one or more silanol compound.

As used herein, a "silanol" or "silanol compound" is a compound that comprises one or more silanol (Si—OH) groups and is commonly a polysiloxane-based polymer that comprises two or more silanol groups, for example a hydroxy-terminated PDMS, among other examples.

In various embodiments, silanol compounds for use in the crosslinkable compositions of the present disclosure include silanol-terminated polymers, such as hydroxy-terminated polysiloxanes, for example,

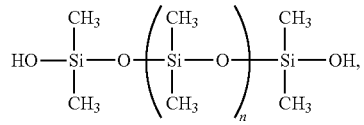

where n is an integer. In certain embodiments, hydroxy-terminated polysiloxanes may be selected which have a weight average molecular weight that is less than 4,000 Daltons.

The crosslinkable compositions described herein, including the crosslinkable compositions formed by any of the above kits or methods, may also optionally contain particles of any material having a diameter ranging from 5 μm or less to 300 μm or more, for example ranging from 5 μm to 10 μm to 25 μm to 50 μm to 100 μm to 300 μm. Such particles may be used to control the distal penetration of the crosslinkable compositions when used as embolics, with penetration distance being controlled based on size. Such particles can be the silica and/or the imaging agent, or may be in addition to them.

The following methods are applicable to any of the compositions of the disclosure and were applied, as indicated, in the Examples below.

Methods.

Rheology:

Formulations were characterized using rheology measurements which were recorded using a TA instruments DHR-1 rheometer using 25 mm sandblasted parallel plates with a Pelletier temperature control system. Testing was conducted at 37° C., and material was loaded at a gap height of 1000 μm. In each characterization, the material was initially "pre-sheared" by running the rheometer in flow mode at a shear rate of 100 per second ($s^{-1}$) for 75 seconds. Following the pre-shear step, three different characterizations were performed:

Hysteresis (Flow) Loop:

A flow ramp increased the shear rate from 1 to 100 $s^{-1}$ over 30 s, the material was held at 100 $s^{-1}$ for 15 s, then the shear rate was decreased from 100 to 1 $s^{-1}$ over 30 s. The material was then conditioned at a shear rate of 10 $s^{-1}$ for 15 s before measuring the material viscosity at 10 $s^{-1}$ for 15 s. Finally, the material was then conditioned at a shear rate of 50 $s^{-1}$ for 15 s before measuring the material viscosity at 50 $s^{-1}$ for 15 s.

Yield Strain:

The material was allowed to recover at low stress (controlled at 0.01 Pa) for 150 s. Subsequently, an amplitude sweep was conducted at constant frequency (1 Hz) ramping the stress from 0.01 to 20.0 Pa.

Shear Recovery:

The material was probed under low strain (2.0%) and low frequency (1 Hz) conditions over time.

Injection Test:

Material injection properties were characterized using an Instron 3343 single column test frame. Final mixed formulations were loaded into a 1 ml syringe and attached to a custom fixture on the test frame. A clinically relevant catheter was attached to the syringe and the distal catheter tip was submerged in a container of 1×PBS warmed to 37° C. The Instron was set to a constant rate of displacement (25 mm/min) and the force was recorded over time using a load cell. A camera was positioned to record the injection of the material into the PBS. The test allows for a direct measure of injection force as well as an assessment of the material properties including the material droplet morphology and coalescence. Droplet morphology can be quantitatively measured using frames from the video and image analysis software, whereas coalescence is qualitatively assessed on a 1-4 scale (termed "QS" score) where 1 is no coalescence noted (clear delineation of boundaries between discrete volumes of material) and 4 is full coalescence (absence of visually discernible boundaries between discrete volumes of material).

Compositions. The compositions listed in Table A below were used in several of the Examples as indicated therein.

TABLE A

|  |  | AMP-1 | | AMP-2 | |
|---|---|---|---|---|---|
|  |  | Component | Wt % | Component | Wt % |
| Phase A | Linear Vinyl PDMS | Vinyl PDMS (5000-10000 Da) | 25.94% | Vinyl PDMS (5000-10000 Da) | 25.94% |
|  | Catalyst | Karstedt's Catalyst (3% Pt) | 0.04% | Karstedt's Catalyst (3% Pt) | 0.04% |
|  | Vinyl Catalyst Modifier | 1,3,5,7-Tetravinyl-1,3,5,7-Tetramethylcyclotetrasiloxane | 0.52% | 1,3,5,7-Tetravinyl-1,3,5,7-Tetramethylcyclotetrasiloxane | 0.52% |
|  | Additive | Sucrose solution (1800 g/L) | 1.00% | Sucrose solution (1800 g/L) | 1.00% |
|  | Filler | Fumed silica (200 $m^2$/g) | 2.50% | Hydrophobic silica (HDMS treated) | 2.50% |
|  | Stabilizer | Silanol (800 Da +− 400 Da) | 2.50% | Silanol (800 Da +− 400 Da) | 2.50% |
|  | Imaging agent | Bismuth Trioxide (80-200 nm) | 17.5% | Bismuth Trioxide (80-200 nm) | 17.5% |
| Phase B | Linear Hydride PDMS 1 | Hydride PDMS (9700 Da) | 7.40% | Hydride PDMS (9700 Da) | 7.40% |
|  | Linear Hydride PDMS 2 | Hydride PDMS (5000 Da) | 5.75% | Hydride PDMS (5000 Da) | 5.75% |
|  | Linear Vinyl PDMS | Vinyl PDMS (5000-10000 Da) | 7.85% | Vinyl PDMS (5000-10000 Da) | 7.85% |
|  | Hydride Crosslinker | Hydride Crosslinker (6900 Da/f ≈ 5) | 5.00% | Hydride Crosslinker (6900 Da/f ≈ 5) | 5.00% |
|  | Additive | TMPEO (1014 Da) | 1.50% | TMPEO (1014 Da) | 1.50% |
|  | Filler | Fumed silica (200 $m^2$/g) | 2.50% | Hydrophobic silica (HDMS treated) | 2.50% |
|  | Stabilizer | Silanol (800 Da +− 400 Da) | 2.50% | Silanol (800 Da +− 400 Da) | 2.50% |
|  | Imaging agent | Bismuth Trioxide (80-200 nm) | 17.5% | Bismuth Trioxide (80-200 nm) | 17.5% |
| Powders | Filler | N/A | N/A | N/A | N/A |
|  | Imaging agent | N/A | N/A | N/A | N/A |
|  |  | AMP-3 | | AMP-4 | |
|  |  | Component | Wt % | Component | Wt % |
| Phase A | Linear Vinyl PDMS | Vinyl PDMS (500-2000 Da) | 31.19% | Vinyl PDMS (5000-10000 Da) | 31.68% |
|  | Catalyst | Karstedt's Catalyst (3% Pt) | 0.05% | Karstedt's Catalyst (3% Pt) | 0.04% |
|  | Vinyl Catalyst Modifier | 1,3,5,7-Tetravinyl-1,3,5,7-Tetramethylcyclotetrasiloxane | 0.26% | 1,3,5,7-Tetravinyl-1,3,5,7-Tetramethylcyclotetrasiloxane | 0.28% |
|  | Additive | N/A | N/A | N/A | N/A |
|  | Filler | N/A | N/A | N/A | N/A |
|  | Stabilizer | N/A | N/A | N/A | N/A |
|  | Imaging agent | N/A | N/A | N/A | N/A |
| Phase B | Linear Hydride PDMS 1 | Hydride PDMS (500-2000 Da) | 20.18% | Hydride PDMS (9700 Da) | 9.11% |
|  | Linear Hydride PDMS 2 | N/A | N/A | Hydride PDMS (5000 Da) | 7.08% |
|  | Linear Vinyl PDMS | N/A | N/A | Vinyl PDMS (5000-10000 Da) | 9.66% |
|  | Hydride Crosslinker | Hydride Crosslinker (1900-2000 Da/f ≈ 4) | 11.32% | Hydride Crosslinker (6900 Da/f ≈ 5) | 6.15% |
|  | Additive | N/A | N/A | N/A | N/A |
|  | Filler | N/A | N/A | N/A | N/A |
|  | Stabilizer | N/A | N/A | N/A | N/A |
|  | Imaging agent | N/A | N/A | N/A | N/A |
| Powders | Filler | Fumed silica (200 $m^2$/g) | 2% | Fumed silica (200 $m^2$/g) | 1% |
|  | Imaging agent | Bismuth Trioxide (80-200 nm) | 35% | Bismuth Trioxide (80-200 nm) | 35% |
|  |  | AMP-5 | | AMP-6 | |
|  |  | Component | Wt % | Component | Wt % |
| Phase A | Linear Vinyl PDMS | Vinyl PDMS (500-2000 Da) | 31.35% | Vinyl PDMS (1600-2400 Da) | 25.19% |
|  | Catalyst | Karstedt's Catalyst (3% Pt) | 0.13% | Karstedt's Catalyst (3% Pt) | 0.62% |
|  | Vinyl Catalyst Modifier | 1,3,5,7-Tetravinyl-1,3,5,7-Tetramethylcyclotetrasiloxane | 0.52% | 1,3,5,7-Tetravinyl-1,3,5,7-Tetramethylcyclotetrasiloxane | 0.20% |
|  | Additive | N/A | N/A | Sucrose solution (1800 g/L) | 1.50% |
|  | Filler | N/A | N/A | Fumed silica (200 $m^2$/g) | 2.50% |
|  | Stabilizer | N/A | N/A | Silanol (800 Da +− 400Da) | 2.50% |
|  | Imaging agent | Bismuth Trioxide (80-200 nm) | 17.5% | Bismuth Trioxide (80-200 nm) | 17.50% |
| Phase B | Linear Hydride PDMS 1 | Hydride PDMS (1250 Da) | 9.53% | Hydride PDMS (1600-2400 Da) | 13.0% |
|  | Linear Hydride PDMS 2 | N/A | N/A | N/A | N/A |
|  | Linear Vinyl PDMS | N/A | N/A | Vinyl PDMS (1600-2400 Da) | 9.0% |
|  | Hydride Crosslinker | Hydride Crosslinker (2500-2600 Da/f ≈ 5) | 22.47% | Hydride Crosslinker (2000 Da/f ≈ 8.5) | 4.0% |
|  | Additive | N/A | N/A | TMPEO (1014 Da) | 1.5% |
|  | Filler | N/A | N/A | Fumed silica (200 $m^2$/g) | 2.5% |
|  | Stabilizer | N/A | N/A | Silanol (800 Da +− 400 Da) | 2.5% |
|  | Imaging agent | Bismuth Trioxide (80-200 nm) | 17.5% | Bismuth Trioxide (80-200 nm) | 17.5% |
| Powders | Filler | Fumed silica (200 $m^2$/g) | 1.00% | N/A | N/A |
|  | Imaging agent | N/A | N/A | N/A | N/A |

TABLE A-continued

|  |  | AMP-7 | | AMP-8 | |
|---|---|---|---|---|---|
|  |  | Component | Wt % | Component | Wt % |
| Phase A | Linear Vinyl PDMS | Vinyl PDMS (1600-2400 Da) | 29.53% | Vinyl PDMS (500-2000 Da) | 31.84% |
|  | Catalyst | Karstedt's Catalyst (3% Pt) | 0.59% | Karstedt's Catalyst (3% Pt) | 0.53% |
|  | Vinyl Catalyst Modifier | 1,3,5,7-Tetravinyl-1,3,5,7-Tetramethylcyclotetrasiloxane | 0.38% | 1,3,5,7-Tetravinyl-1,3,5,7-Tetramethylcyclotetrasiloxane | 0.13% |
|  | Additive | Water | 3.0% | N/A | N/A |
|  | Filler | N/A | N/A | N/A | N/A |
|  | Stabilizer | N/A | N/A | N/A | N/A |
|  | Imaging agent | N/A | N/A | Bismuth Trioxide (80-200 nm) | 17.50% |
| Phase B | Linear Hydride PDMS 1 | Hydride PDMS (1600-2400 Da) | 18.6% | Hydride PDMS (1250 Da) | 8.16% |
|  | Linear Hydride PDMS 2 | N/A | N/A | N/A | N/A |
|  | Linear Vinyl PDMS | Vinyl PDMS (1600-2400 Da) | 8.1% | N/A | N/A |
|  | Hydride Crosslinker | Hydride Crosslinker (2000 Da/f ≈ 8.5) | 3.8% | Hydride Crosslinker (2500-2600 Da/f ≈ 5) | 22.82% |
|  | Additive | N/A | N/A | TMPEO (1014 Da) | 0.51% |
|  | Filler | N/A | N/A | N/A | N/A |
|  | Stabilizer | N/A | N/A | N/A | N/A |
|  | Imaging agent | N/A | N/A | Bismuth Trioxide (80-200 nm) | 17.50% |
| Powders | Filler | Fumed silica (200 m²/g) | 1.00% | Fumed silica (200 m²/g) | 1.00% |
|  | Imaging agent | Bismuth Trioxide (80-200 nm) | 35% | N/A | N/A |

|  |  | AMP-9 | | AMP-10 | |
|---|---|---|---|---|---|
|  |  | Component | Wt % | Component | Wt % |
| Phase A | Linear Vinyl PDMS | Vinyl PDMS (500-2000 Da) | 31.35% | Vinyl PDMS (1600-2400 Da) | 29.72% |
|  | Catalyst | Karstedt's Catalyst (3% Pt) | 0.52% | Karstedt's Catalyst (3% Pt) | 0.62% |
|  | Vinyl Catalyst Modifier | 1,3,5,7-Tetravinyl-1,3,5,7-Tetramethylcyclotetrasiloxane | 0.13% | 1,3,5,7-Tetravinyl-1,3,5,7-Tetramethylcyclotetrasiloxane | 0.32% |
|  | Additive | N/A | N/A | N/A | N/A |
|  | Filler | Fumed silica (200 m²/g) | 0.50% | Hydrophobic silica (HDMS treated) | 1.00% |
|  | Stabilizer | N/A | N/A | Silanol (800 Da +− 400 Da) | 1.00% |
|  | Imaging agent | N/A | N/A | Bismuth Trioxide (80-200 nm) | 17.50% |
| Phase B | Linear Hydride PDMS 1 | Hydride PDMS (1250 Da) | 9.53% | Hydride PDMS (1600-2400 Da) | 8.00% |
|  | Linear Hydride PDMS 2 | N/A | N/A | N/A | N/A |
|  | Linear Vinyl PDMS | N/A | N/A | Vinyl PDMS (1600-2400 Da) | 13.84% |
|  | Hydride Crosslinker | Hydride Crosslinker (2500-2600 Da/f ≈ 5) | 22.47% | Hydride Crosslinker (2000 Da/f ≈ 8.5) | 7.00% |
|  | Additive | N/A | N/A | TMPEO (1014 Da) | 1.50% |
|  | Filler | Fumed silica (200 m²/g) | 0.50% | Hydrophobic silica (HDMS treated) | 1.00% |
|  | Stabilizer | N/A | N/A | Silanol (800 Da +− 400 Da) | 1.00% |
|  | Imaging agent | N/A | N/A | Bismuth Trioxide (80-200 nm) | 17.50% |
| Powders | Filler | N/A | N/A | N/A | N/A |
|  | Imaging agent | Bismuth Trioxide (80-200 nm) | 35.00% | N/A | N/A |

|  |  | AMP-11 | | AMP-12 | |
|---|---|---|---|---|---|
|  |  | Component | Wt % | Component | Wt % |
| Phase A | Linear Vinyl PDMS | Vinyl PDMS (1600-2400 Da) | 30.40% | Vinyl PDMS (500-2000 Da) | 31.67% |
|  | Catalyst | Karstedt's Catalyst (3% Pt) | 0.62% | Karstedt's Catalyst (3% Pt) | 0.53% |
|  | Vinyl Catalyst Modifier | 1,3,5,7-Tetravinyl-1,3,5,7-Tetramethylcyclotetrasiloxane | 0.48% | 1,3,5,7-Tetravinyl-1,3,5,7-Tetramethylcyclotetrasiloxane | 0.05% |
|  | Additive | N/A | N/A | N/A | N/A |
|  | Filler | N/A | N/A | N/A | N/A |
|  | Stabilizer | N/A | N/A | N/A | N/A |
|  | Imaging agent | Bismuth Trioxide (80-200 nm) | 35.00% | N/A | N/A |
| Phase B | Linear Hydride PDMS 1 | Hydride PDMS (1600-2400 Da) | 12.50% | Hydride PDMS (500-2000 Da) | 20.66% |
|  | Linear Hydride PDMS 2 | N/A | N/A | N/A | N/A |
|  | Linear Vinyl PDMS | Vinyl PDMS (1600-2400 Da) | 8.00% | N/A | N/A |
|  | Hydride Crosslinker | Hydride Crosslinker (2000 Da/f ≈ 8.5) | 7.50% | Hydride Crosslinker (1900-2000 Da/f ≈ 4) | 11.59% |
|  | Additive | TMPEO (1014 Da) | 1.50% | N/A | N/A |
|  | Filler | Fumed silica (200 m²/g) | 2.00% | N/A | N/A |
|  | Stabilizer | Silanol (800 Da +− 400 Da) | 2.00% | N/A | N/A |
|  | Imaging agent | N/A | N/A | N/A | N/A |
| Powders | Filler | N/A | N/A | Fumed silica (200 m²/g) | 0.50% |
|  | Imaging agent | N/A | N/A | Bismuth Trioxide (80-200 nm) | 35% |

TABLE A-continued

|  |  | AMP-13 | | AMP-14 | |
|---|---|---|---|---|---|
|  |  | Component | Wt % | Component | Wt % |
| Phase A | Linear Vinyl PDMS | Vinyl PDMS (500-2000 Da) | 31.43% | Vinyl PDMS (500-2000 Da) | 31.30% |
|  | Catalyst | Karstedt's Catalyst (3% Pt) | 0.52% | Karstedt's Catalyst (3% Pt) | 0.52% |
|  | Vinyl Catalyst Modifier | 1,3,5,7-Tetravinyl-1,3,5,7-Tetramethylcyclotetrasiloxane | 0.05% | 1,3,5,7-Tetravinyl-1,3,5,7-Tetramethylcyclotetrasiloxane | 0.05% |
|  | Additive | N/A | N/A | N/A | N/A |
|  | Filler | N/A | N/A | N/A | N/A |
|  | Stabilizer | N/A | N/A | N/A | N/A |
|  | Imaging agent | N/A | N/A | N/A | N/A |
| Phase B | Linear Hydride PDMS 1 | Hydride PDMS (500-2000 Da) | 20.50% | Hydride PDMS (500-2000 Da) | 20.42% |
|  | Linear Hydride PDMS 2 | N/A | N/A | N/A | N/A |
|  | Linear Vinyl PDMS | N/A | N/A | N/A | N/A |
|  | Hydride Crosslinker 0 | Hydride Crosslinker (1900-2000 Da/f ≈ 4) | 11.50% | Hydride Crosslinker (1900-2000 Da/f ≈ 4) | 11.45% |
|  | Additive | N/A | N/A | N/A | N/A |
|  | Filler | N/A | N/A | N/A | N/A |
|  | Stabilizer | N/A | N/A | N/A | N/A |
|  | Imaging agent | N/A | N/A | N/A | N/A |
| Powders | Filler | Fumed silica (200 $m^2/g$) | 1.00% | Fumed silica (200 $m^2/g$) | 1.25% |
|  | Imaging agent | Bismuth Trioxide (80-200 nm) | 35.00% | Bismuth Trioxide (80-200 nm) | 35% |

|  |  | AMP-15 | | AMP-16 | |
|---|---|---|---|---|---|
|  |  | Component | Wt % | Component | Wt % |
| Phase A | Linear Vinyl PDMS | Vinyl PDMS (500-2000 Da) | 30.94% | Vinyl PDMS (500-2000 Da) | 29.95% |
|  | Catalyst | Karstedt's Catalyst (3% Pt) | 0.52% | Karstedt's Catalyst (3% Pt) | 0.50% |
|  | Vinyl Catalyst Modifier | 1 3 5 7-Tetravinyl-1,3,5,7-Tetramethylcyclotetrasiloxane | 0.05% | 1 3 5 7-Tetravinyl-1,3,5,7-Tetramethylcyclotetrasiloxane | 0.05% |
|  | Additive | N/A | N/A | N/A | N/A |
|  | Filler | N/A | N/A | N/A | N/A |
|  | Stabilizer | N/A | N/A | N/A | N/A |
|  | Imaging agent | N/A | N/A | N/A | N/A |
| Phase B | Linear Hydride PDMS 1 | Hydride PDMS (500-2000 Da) | 20.18% | Hydride PDMS (500-2000 Da) | 19.54% |
|  | Linear Hydride PDMS 2 | N/A | N/A | N/A | N/A |
|  | Linear Vinyl PDMS | N/A | N/A | N/A | N/A |
|  | Hydride Crosslinker 0 | Hydride Crosslinker (1900-2000 Da/f ≈ 4) | 11.32% | Hydride Crosslinker (1900-2000 Da/f ≈ 4) | 10.96% |
|  | Additive | N/A | N/A | N/A | N/A |
|  | Filler | N/A | N/A | N/A | N/A |
|  | Stabilizer | N/A | N/A | N/A | N/A |
|  | Imaging agent | N/A | N/A | N/A | N/A |
| Powders | Filler | Fumed silica (200 $m^2/g$) | 2.00% | Fumed silica (200 $m^2/g$) | 4.00% |
|  | Imaging agent | Bismuth Trioxide (80-200 nm) | 35% | Bismuth Trioxide (80-200 nm) | 35% |

|  |  | AMP-17 | | AMP-18 | |
|---|---|---|---|---|---|
|  |  | Component | Wt % | Component | Wt % |
| Phase A | Linear Vinyl PDMS | Vinyl PDMS (5000-10000 Da) | 31.66% | Vinyl PDMS (5000-10000 Da) | 31.41% |
|  | Catalyst | Karstedt's Catalyst (3% Pt) | 0.55% | Karstedt's Catalyst (3% Pt) | 0.55% |
|  | Vinyl Catalyst Modifier | 1,3,5,7-Tetravinyl-1,3,5,7-Tetramethylcyclotetrasiloxane | 0.04% | 1,3,5,7-Tetravinyl-1,3,5,7-Tetramethylcyclotetrasiloxane | 0.04% |
|  | Additive | N/A | N/A | N/A | N/A |
|  | Filler | N/A | N/A | N/A | N/A |
|  | Stabilizer | N/A | N/A | N/A | N/A |
|  | Imaging agent | N/A | N/A | N/A | N/A |
| Phase B | Linear Hydride PDMS 1 | Hydride PDMS (9700 Da) | 9.18% | Hydride PDMS (9700 Da) | 9.11% |
|  | Linear Hydride PDMS 2 | Hydride PDMS (5000 Da) | 7.14% | Hydride PDMS (5000 Da) | 7.08% |
|  | Linear Vinyl PDMS | Vinyl PDMS (5000-10000 Da) | 9.74% | Vinyl PDMS (5000-10000 Da) | 9.66% |
|  | Hydride Crosslinker | Hydride Crosslinker (6900 Da/f ≈ 5) | 6.20% | Hydride Crosslinker (6900 Da/f ≈ 5) | 6.15% |
|  | Additive | N/A | N/A | N/A | N/A |
|  | Filler | N/A | N/A | N/A | N/A |
|  | Stabilizer | N/A | N/A | N/A | N/A |
|  | Imaging agent | N/A | N/A | N/A | N/A |
| Powders | Filler | Fumed silica (200 $m^2/g$) | 0.50% | Fumed silica (200 $m^2/g$) | 1.00% |
|  | Imaging agent | Bismuth Trioxide (80-200 nm) | 35% | Bismuth Trioxide (80-200 nm) | 35% |

TABLE A-continued

| | | AMP-19 | | AMP-20 | |
|---|---|---|---|---|---|
| | | Component | Wt % | Component | Wt % |
| Phase A | Linear Vinyl PDMS | Vinyl PDMS (5000-10000 Da) | 30.92% | Vinyl PDMS (5000-10000 Da) | 30.43% |
| | Catalyst | Karstedt's Catalyst (3% Pt) | 0.54% | Karstedt's Catalyst (3% Pt) | 0.53% |
| | Vinyl Catalyst Modifier | 1,3,5,7-Tetravinyl-1,3,5,7-Tetramethylcyclotetrasiloxane | 0.04% | 1,3,5,7-Tetravinyl-1,3,5,7-Tetramethylcyclotetrasiloxane | 0.04% |
| | Additive | N/A | N/A | N/A | N/A |
| | Filler | N/A | N/A | N/A | N/A |
| | Stabilizer | N/A | N/A | N/A | N/A |
| | Imaging agent | N/A | N/A | N/A | N/A |
| Phase B | Linear Hydride PDMS 1 | Hydride PDMS (9700 Da) | 8.97% | Hydride PDMS (9700 Da) | 8.83% |
| | Linear Hydride PDMS 2 | Hydride PDMS (5000 Da) | 6.97% | Hydride PDMS (5000 Da) | 6.86% |
| | Linear Vinyl PDMS | Vinyl PDMS (5000-10000 Da) | 9.51% | Vinyl PDMS (5000-10000 Da) | 9.36% |
| | Hydride Crosslinker | Hydride Crosslinker (6900 Da/f ≈ 5) | 6.05% | Hydride Crosslinker (6900 Da/f ≈ 5) | 5.96% |
| | Additive | N/A | N/A | N/A | N/A |
| | Filler | N/A | N/A | N/A | N/A |
| | Stabilizer | N/A | N/A | N/A | N/A |
| | Imaging agent | N/A | N/A | N/A | N/A |
| Powders | Filler | Fumed silica (200 m$^2$/g) | 2.00% | Fumed silica (200 m$^2$/g) | 3.00% |
| | Imaging agent | Bismuth Trioxide (80-200 nm) | 35% | Bismuth Trioxide (80-200 nm) | 35% |

Example 1. Two Phase Formulation Containing Components with MW 5,000-10,000 Da and Hydrophilic Silica A two phase formulation (phase A and phase B, both liquid phases) were prepared as formulated in Table 1.

TABLE 1

| Component | Weight % |
|---|---|
| Phase A | |
| Vinyl PDMS (6500 Da) | 51.87% |
| Silanol PDMS (550 Da) | 5.00% |
| Modifier for Pt | 0.08% |
| Catalyst | 1.05% |
| Physical Crosslinker | 2.00% |
| Fumed Silica | 5.00% |
| Bismuth Oxide | 35.00% |
| Phase B | |
| Linear Hydride (10550 Da) | 11.50% |
| Linear Hydride (5273 Da) | 14.80% |
| Silanol PDMS (550 Da) | 5.00% |
| Hydride Crosslinker (7250 Da) | 10.00% |
| Physical Crosslinker (1014 Da) | 3.00% |
| Linear Vinyl (6500 Da) | 15.70% |
| Fumed Silica | 5.00% |
| Bismuth Oxide | 35.00% |

A crosslinkable formulation was formed by combining phase A and phase B and properties of the same were measured and shown in Table 2. Methods by which viscosity (as measured by oscillatory rheology at 0.1 Hz and 1% strain at 25° C.), gel time and injection force were measured are described above.

TABLE 2

| Property | Value |
|---|---|
| Viscosity | 297 Pa*s |
| Gel time | 6 minutes |
| Injection Force | 23 lbf |

Example 2. Two Phase Formulation Containing Components with MW 5,000-11,000 Da and Hydrophobic Silica (Silica Treated with Hexamethyldisilazane)

A two phase formulation (phase A and phase B, both liquid phases) was prepared as formulated in Table 3.

TABLE 3

| Component | Weight % |
|---|---|
| Phase A | |
| Vinyl PDMS (6500 Da) | 51.87% |
| Silanol PDMS (550 Da) | 5.00% |
| Modifier for Pt | 0.08% |
| Catalyst | 1.05% |
| Physical Crosslinker | 2.00% |
| HMDS Treated Fumed Silica | 5.00% |
| Bismuth Oxide | 35.00% |
| Phase B | |
| Linear Hydride (10550 Da) | 11.50% |
| Linear Hydride (5273 Da) | 14.80% |
| Silanol PDMS (550 Da) | 5.00% |
| Hydride Crosslinker (7250 Da) | 10.00% |
| Physical Crosslinker (1014 Da) | 3.00% |
| Linear Vinyl (6500 Da) | 15.70% |
| HMDS Treated Fumed Silica | 5.00% |
| Bismuth Oxide | 35.00% |

A crosslinkable formulation was formed by combining phase A and phase B and properties of the same were measured and shown in Table 4.

TABLE 4

| Property | Value |
|---|---|
| Viscosity | 997 Pa*s |
| Gel time | 7.2 min |
| Injection Force | 27 lbf |

Example 3. Simplified Two Phase Formulation Containing Components with MW 5,000-10,000 Da and Hydrophilic Silica A two phase formulation (phase A and phase B, both fluid phases) was prepared as formulated in Table 5.

TABLE 5

| Component | Weight % |
|---|---|
| Phase A | |
| Vinyl PDMS (6500 Da) | 53.85% |
| Modifier for Pt | 0.10% |
| Catalyst | 1.05% |
| Physical Crosslinker | 3.00% |
| Fumed Silica | 7.00% |
| Bismuth Oxide | 35.00% |
| Phase B | |
| Hydride Crosslinker (7250 Da) | 29.00% |
| Physical Crosslinker | 3.00% |
| Linear Vinyl | 26.00% |
| Fumed Silica | 7.00% |
| Bismuth Oxide | 35.00% |

A crosslinkable formulation was formed by combining phase A and phase B and properties of the same were measured and shown in Table 6.

TABLE 6

| Property | Value |
|---|---|
| Viscosity | 10 Pa*s |
| Gel time | 8.0 min |
| Injection Force | Unknown |

Example 4. Formulation Composed of Components with MW 5,000-10,000 Da in which Dry and Fluid Components are Mixed at the Time of Administration A formulation was prepared as shown in Table 7. Phase A and Phase B were made separately. The formulation was then made by mixing Phase A and Phase B with the dry components (i.e., fumed silica and bismuth oxide).

TABLE 7

| Component | Weight % |
|---|---|
| Phase A | |
| Vinyl PDMS (6500 Da) | 62.81% |
| Modifier for Pt | 0.08% |
| Catalyst | 1.10% |
| Phase B | |
| Linear Hydride (10550 Da) | 18.21% |
| Linear Hydride (5273 Da) | 14.15% |
| Hydride Crosslinker (7250 Da) | 12.31% |
| Linear Vinyl (6500 Da) | 19.32% |
| Combination of Phase A, Phase B, and dry components | |
| Phase A | 32.00% |
| Phase B | 32.00% |
| Fumed Silica | 1.00% |
| Bismuth Oxide | 35.00% |

A crosslinkable formulation was formed by combining phase A, phase B, and dry components and properties of the same were measured and shown in Table 8.

TABLE 8

| Property | Value |
|---|---|
| Viscosity | 833 Pa*s |
| Gel time | 5.6 min |
| Injection Force | 18.4 lbf |

Example 5. Simplified Formulation Composed of Lower MW Polymers (Less than 2100 Da) in which Dry and Fluid Components are Mixed at the Time of Administration A formulation was prepared as shown in Table 9. Phase A and Phase B were made separately. The formulation was then made by mixing Phase A and Phase B with the dry components (i.e., fumed silica and bismuth oxide).

TABLE 9

| Component | Weight % |
|---|---|
| Phase A | |
| Vinyl PDMS (800 Da) | 61.87% |
| Modifier for Pt | 0.10% |
| Catalyst | 1.03% |
| Phase B | |
| Linear Hydride (1050 Da) | 40.36% |
| Hydride Crosslinker (1950 Da) | 22.64% |
| Combination of Phase A, Phase B, and dry components | |
| Phase A | 31.50% |
| Phase B | 31.50% |
| Fumed Silica | 2.00% |
| Bismuth Oxide | 35.00% |

A crosslinkable formulation was formed by combining phase A, phase B, and dry components and properties of the same were measured and shown in Table 10.

TABLE 10

| Property | Value |
|---|---|
| Viscosity | 3634.18 Pa*s |
| Gel time | 5.9 min |
| Injection Force | 6.29 lbf |

Example 6. In Vivo Chronic Study

A pilot chronic study was performed in which a single pole of each kidney in three swine were embolized using a crosslinkable composition of Example 1 and the animals survived to either 30 or 90 days to assess penetration into vessels, occlusion performance, and histopathology. FIGS. 3A-3C demonstrate the shear-thinning properties and behavior of the crosslinkable composition during the embolization. The crosslinkable composition initially exits the catheter (catheter is illustrated by the upper arrow in each of FIGS. 3A-3C) as a continuous stream as shown by the lower arrow in FIG. 3A. As the crosslinkable composition flows more distally and encounters higher shear, the crosslinkable composition responds and adapts by separating into discrete volumes that exhibit deep penetration within the branches (see FIG. 3B, lower left arrow). As injection continues, the crosslinkable composition coalesces into a solid and complete cast that fills the entire volume of the vessel to provide complete occlusion (see FIG. 3C). Gross images of the kidney at 90 days showed significant tissue shrinkage as a result of being embolized (FIG. 3D). As determined by angiography, there was no evidence of recanalization at either 30 or 90 days. X-ray images of the crosslinkable composition showed good distal penetration (see FIG. 3E). MicroCT scanning presented with minimal imaging artefact and confirmed that the crosslinkable composition penetrated and occluded vessels of <100 micron diameter (see FIG. 3F). Moreover, the material was sufficiently radiopaque, which allowed for real-time visualization during the embolization procedure.

Example 7. Crosslinkable Composition Biocompatibility

The embolized kidneys of the above pilot study were prepared for histopathological analysis via hematoxylin & eosin staining to evaluate inflammation, vessel injury, necrosis, and hemorrhage. Scoring was performed on a graded scale from 0 to 3 (none, minimal, mild/moderate, and severe) as described in Sabareesh Kumar, N., et al., Histopathological changes in brain arteriovenous malformations after embolization using Onyx or N-butyl cyanoacrylate. *Journal of Neurosurgery JNS*, 2009. 111(1): p. 105-113 and Siskin, G. P., et al., Pathologic Evaluation of a Spherical Polyvinyl Alcohol Embolic Agent in a Porcine Renal Model. *Journal of Vascular and Interventional Radiology*, 2003. 14(1): p. 89-98. The results show the absence of vessel injury, necrosis, and only minimal to mild inflammation, indicating a good biocompatibility profile at both time-points. See Table 11, FIG. 4A (showing histopathology results at 30 days), and FIG. 4B (showing histopathology results at 90 days).

TABLE 11

Histological scoring summary.

| Cohort | Vessel Injury | Inflammation | Necrosis | Hemorrhage |
|---|---|---|---|---|
| 30 d | 0 | 2 | 0 | 1 |
| 90 d | 0 | 1.5 | 0.5 | 0.5 |

Example 8. Further Observations

Viscosity (as measured by oscillatory rheology at 0.1 Hz and 1% strain at 25° C.) and injection force were measured for the following (a) a polymer formulation like that of Example 4 but without catalyst and catalyst modifier, (b) the polymer formulation of (a) with 1% silica added, (c) the polymer formulation of (a) with 1.5% silica added, (d) the polymer formulation of (a) with 35% bismuth oxide added, and (e) the polymer formulation of (a) with 35% bismuth oxide and 1% silica added. The results are presented in FIG. 5. As seen from FIG. 5, approximately a 10× increase in viscosity is seen with either silica (1%) or bismuth oxide (35%) alone, and approximately a 2800× increase in viscosity is seen when silica and bismuth oxide are formulated together, with a relatively small accompanying increase in injection force.

Example 9. Impact of Preparation and Order of Addition on Material Properties

Figure 6:
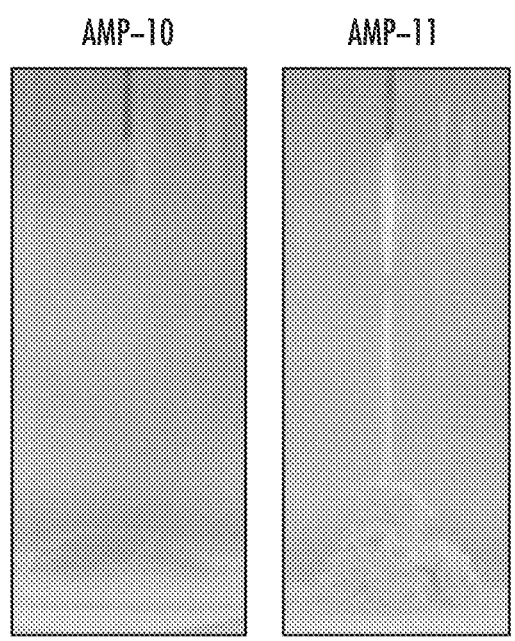
FIG. 6 shows the impact of the preparation method of two compositions of the disclosure on coalescence of the compositions.

Two compositions, AMP-10 and AMP-11 (Table A), which have the same formulation at the same concentrations for a majority of the components were prepared using different methods of the disclosure. As shown in FIG. 6, the different preparation methods resulted in significantly different behavior in the PBS injection test (described below). AMP-10 exits the catheter as a droplet and exhibits material coalescence while AMP-11 exits the catheter as an extruded droplet that does not coalesce. These different behaviors ultimately impact performance in vivo (e.g., degree of distal penetration, completeness of casting, proximal reflux, vessel spasms or vessel constriction) and highlight the impact of preparation of the same components on material properties. The difference in preparation is as follows: AMP-10 was prepared with silica and bismuth equally distributed and compounded in Phase A and Phase B; for AMP-11, 100% of the silica was compounded into Phase B while 100% of the bismuth trioxide was compounded into Phase A.

Material injection properties were characterized using an Instron 3343 single column test frame. Final mixed formulations were loaded into a 1 ml syringe and attached to a custom fixture on the test frame. A clinically relevant catheter (0.021" catheter) was attached to the syringe and the distal catheter tip was submerged in a container of 1×PBS warmed to 37° C. The Instron was set to a constant rate of displacement (25 mm/min) and the force was recorded over time using a load cell. A camera was positioned to record the injection of the material into the PBS. The test allows for a direct measure of injection force as well as an assessment of the material properties including the material droplet morphology and the coalescence. Droplet morphology is quantitatively measured using frames from the video and image analysis software, whereas coalescence is qualitatively assessed on a 1-4 scale (termed "QS" score) where 1 is no coalescence noted (clear delineation of boundaries between discrete volumes of material) and 4 is full coalescence (absence of visually discernible boundaries between discrete volumes of material).

Example 10. Impact of Preparation and Order of Addition on Material Properties: Composition Made at Time of Injection Vs. Pre-Wet Silica Vs. Pre-Wet Bismuth Three compositions were prepared in order to examine the impact of pre-wetting either silica (AMP-9) or bismuth (AMP-5) relative to a composition in which neither bismuth or silica is pre-wet (AMP-13). See Table A for compositions. All formulations were subjected to a PBS injection assay as described in Example 9.

Figure 7:
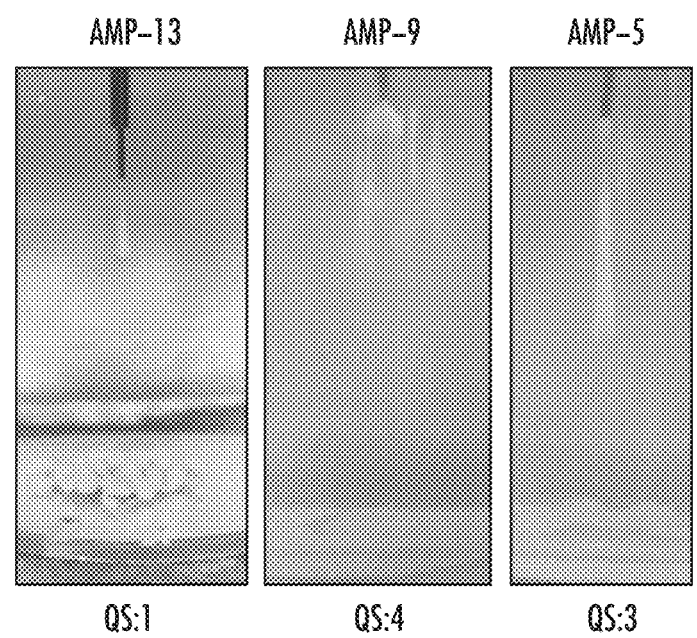
FIG. 7 shows the impact of pre-wetting silica or bismuth on coalescence of the compositions of the disclosure relative to a composition where neither silica nor bismuth is pre-wetted.

As can be seen in FIG. 7, the different preparation methods resulted in significantly different behavior in the PBS injection assay test. The formulation in which neither the silica nor bismuth was pre-wetted (AMP-13) exits the catheter as a slightly elongated droplet that has poor coalescence (QS of 1). When the silica in this system was pre-wetted at 70° C. for 3 days (AMP-9), the material exits the catheter as a rounded droplet with good coalescence (QS of 4). In the formulation in which only the bismuth was pre-wetted (AMP-5), the material exits the catheter as an elongated droplet with a QS of 3. These data demonstrate that different extrusion and coalescence behaviors are obtained by wetting the silica or bismuth components. These different behaviors impact performance in vivo including presence of proximal reflux, distal penetration, and completeness of casting and highlight the impact of preparation of the same components on material properties.

Figure 8:
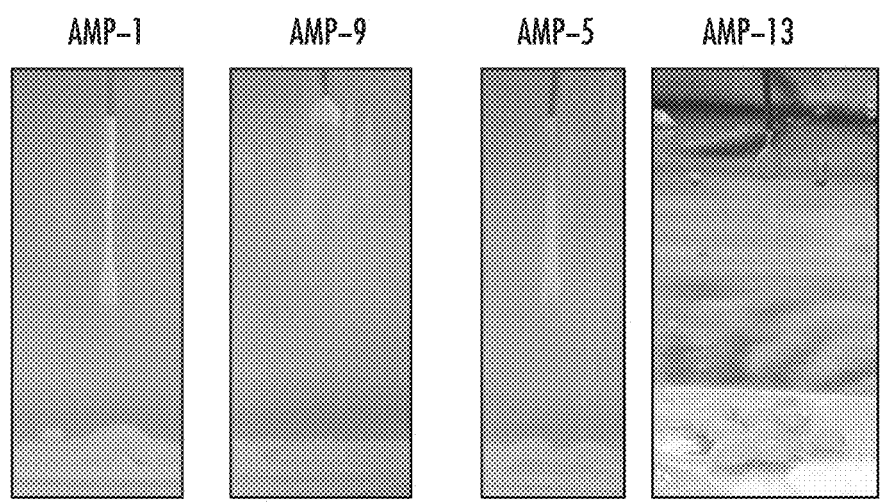
FIG. 8 shows the impact on the coalescence of pre-wetting either silica or bismuth relative to a composition in which both bismuth and silica are pre-wet and a composition in which neither silica or bismuth are pre-wet.
Figure 9A:
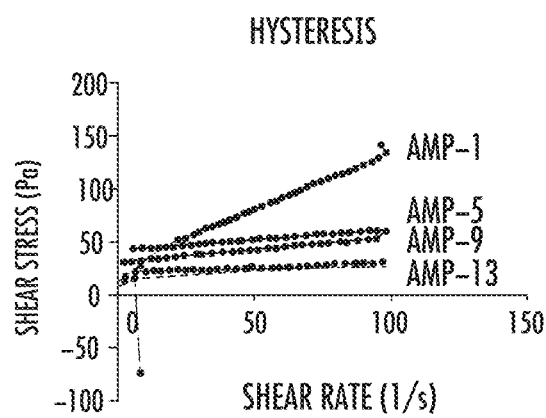
FIG. 9 shows the impact of pre-wetting either silica or bismuth relative to a composition in which both bismuth and silica are pre-wet and a composition in which neither silica or bismuth are pre-wet on the plastic viscosity (slope of the hysteresis curve)(FIG. 9A), shear recovery of the compositions (FIG. 9B), storage modulus (FIG. 9C), and ductility elongation curve (FIG. 9D).
Figure 9B:
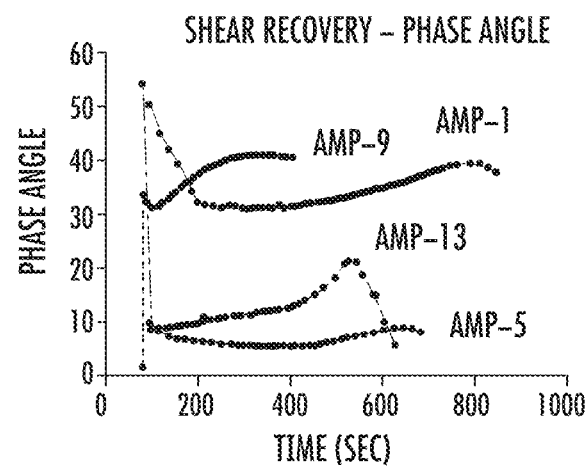
Figure 9C:
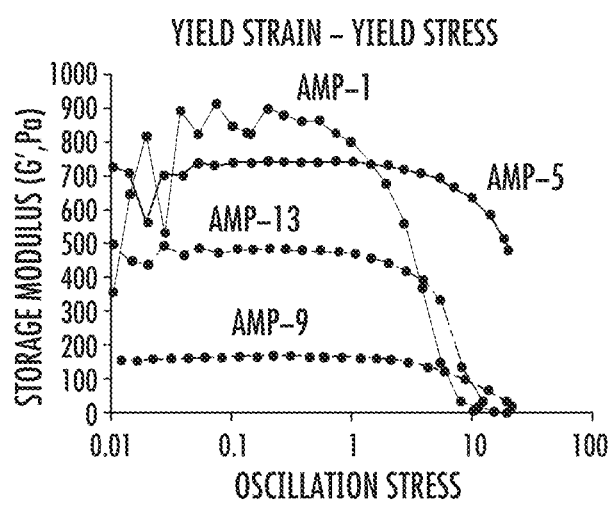
Figure 9D:
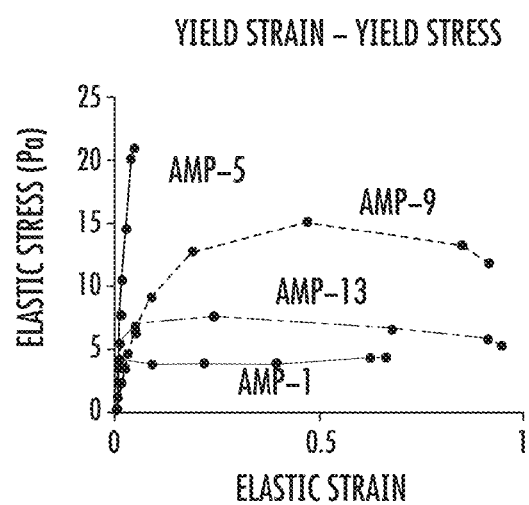

Example 11. Impact of Preparation and Order of Addition on Material Properties The impact of pre-wetting either silica (AMP-9) or bismuth (AMP-5) relative to a composition in which both bismuth and silica are pre-wet (AMP-1) and a composition in which neither silica or bismuth are pre-wet (AMP-13) on the rheological properties of the compositions was examined. The results are shown in FIG. 8, which illustrate the range of properties that can be achieved with respect to extrusion behavior in the PBS injection assay and rheologically via hysteresis curve, yield strain-yield stress curve, yield strain-ductility curve, and shear recovery-phase angle curve. A brief description highlighting these properties follows:

In a pre-formulated system where both the silica and bismuth are both wetted and annealed (AMP-1), the material exhibits viscoelastic fluid behavior with a QS of 4 (or good coalescence) in the injection test, FIG. 8. Rheologically, the material has a high plastic viscosity (slope of the hysteresis curve), storage modulus of ~900 Pa at <1 Pa stress, ductile elongation curve, and a phase angle >45 degrees immediately after being sheared. (FIG. 9.)

In a system where only the bismuth trioxide is pre-wet and annealed (AMP-5), the material behaves as an elastoplastic solid. Rheologically, this is observed via its elongation curve, which has a high slope with little ability to plastically deform and a low phase angle of ~10 degrees immediately after being sheared. AMP-9 shows the impact of pre-wetting silica instead of the bismuth trioxide on material behavior. Here, the material behaves as a droplet as it exits the catheter in the injection test. Rheologically, the material has a much lower storage modulus than AMP-5 (160 vs. 740 Pa, respectively), exhibits ductility, and has a phase angle of >30 degrees.

Finally, in a system where neither the silica or the imaging agent are wetted or annealed (AMP-13), the material exits the catheter as a droplet with poor coalescence (QS: 1) that is rheologically more of a solid-like material, as evidenced by a <10 degree phase angle.

Example 12. Impact of Imaging Agent Dispersion on Injectability and Vessel Spasm The impact of particle dispersion of a radiopaque agent in the compositions of the disclosure on injection force and in vivo performance was examined.

Figure 10A:
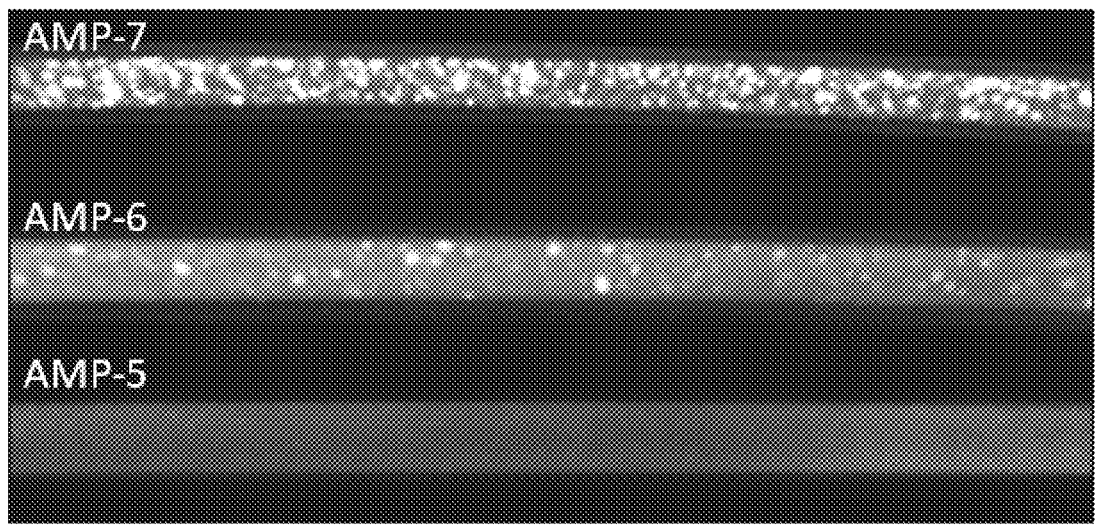
FIG. 10A shows the impact of imaging agent (bismuth trioxide) dispersion in various compositions on injection force.
Figure 10B:
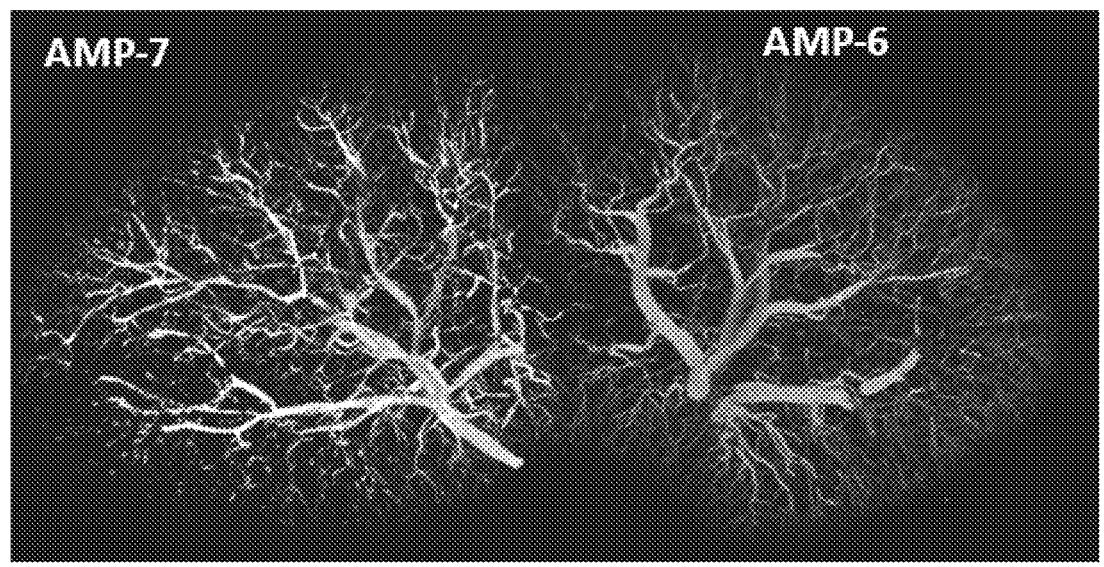
FIG. 10B shows the effect of imaging agent particle dispersion on vessel constriction and casting of the compositions to the distal branches of swine kidney upon injection.
Figure 10C:
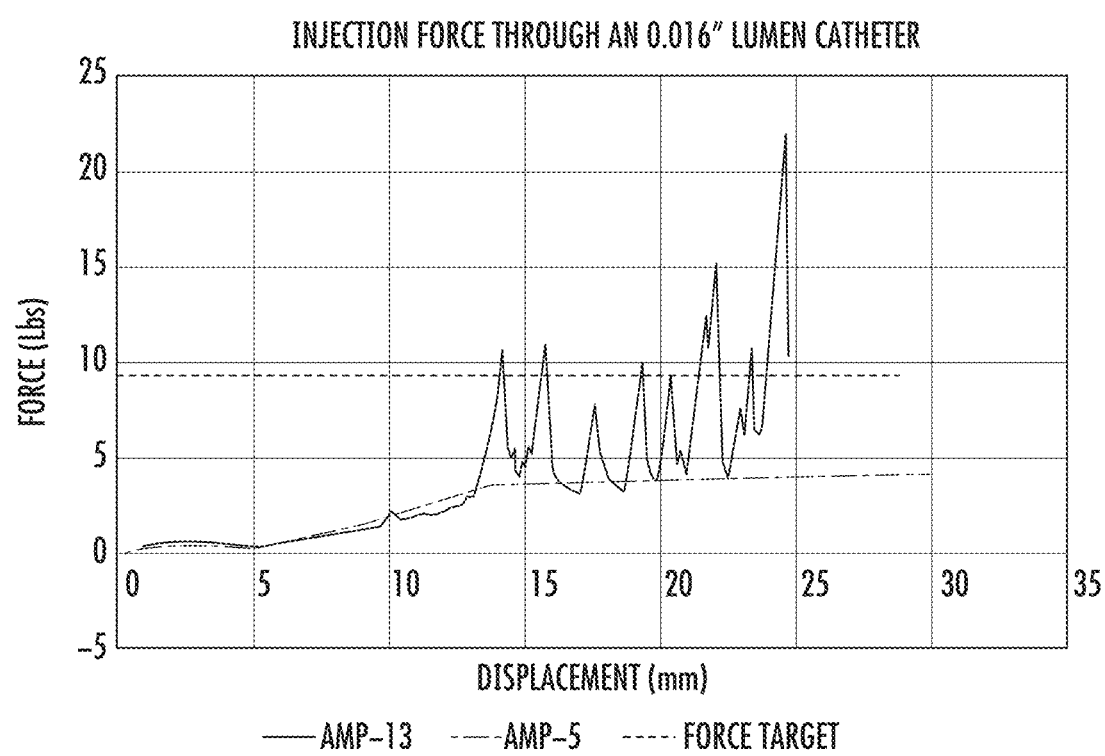
FIG. 10C shows the effect of imaging agent dispersion on injection force.

Formulations representing different preparation methods of the disclosure were made (AMP-5, AMPp-6, and AMP-7, Table A). The compositions were each injected through a catheter into a 1 mm inner diameter silicone tube and then imaged using uCT. Radiopaque agent dispersion was qualitatively assessed using uCT reconstructions with a voxel resolution of 15 um, FIG. 10A. As can be seen, the mixing of dry powders at the time of injection (AMP-7) results in larger and less disperse radiopaque agent particles compared to formulations where the radiopaque agent is compounded into the polymer (AMP-5 and AMP-6). Without being held to any theory, it appears that the particles are more fully wetted in AMP-5 and AMP-6 compared to the composition which is mixed at the time of injection (AMP-7), which results in better dispersion of the particles as evidenced by a reduction in number of observed agglomerates. The significance of the dispersion of the radiopaque agent is shown in FIG. 10B where AMP-6 and AMP-7 were injected into the same kidney of a swine. It can be seen that AMP-7 has fewer dispersed radiopaque agent particles and resulted in both vessel constriction as well as a lack of casting the very distal branches compared to AMP-6. The larger particles are thought to irritate the endothelium resulting in constriction. In addition, imaging agent dispersion has been shown to increase injection force when using the injection test method (described above) (FIG. 10C), especially in smaller catheter lumens such as 0.016" where the larger less disperse particles present when powders are introduced dry (AMP-13; upper curve) may encourage clumping and clogging of the catheter lumen when compared to pre-wet particles (AMP-5; lower curve).

Injection test method: Injection was done using a 1 ml syringe at a constant rate of 0.5 ml/min. through a length of 100 cm of a 0.016" catheter.

Example 13. Impact of Mixing Silica at Time of Injection

Figure 11:
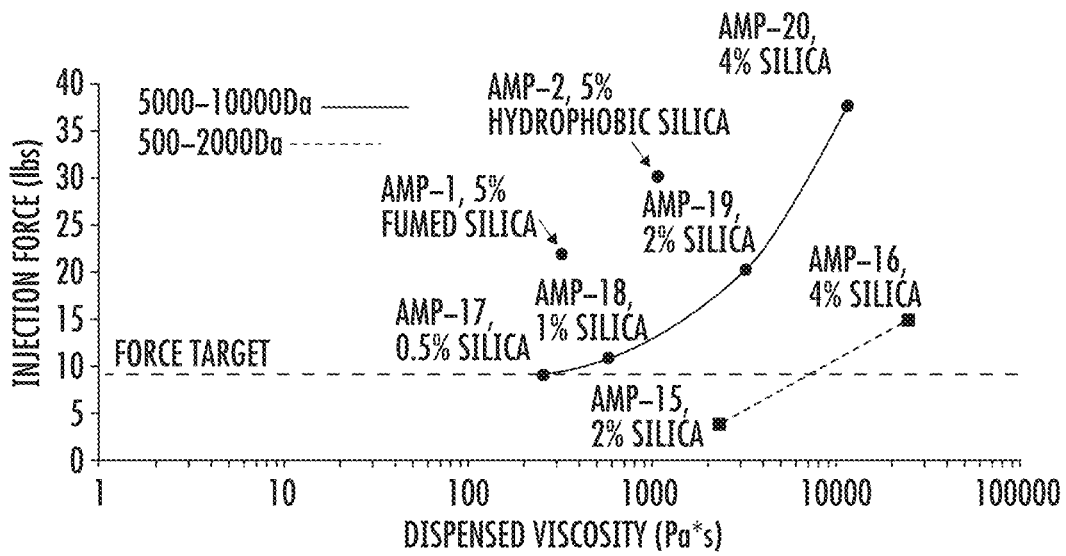
FIG. 11 shows injection force data gathered from the injection test method versus viscosity as measured using low frequency oscillatory rheology comparing formulations where the powders were compounded into the polymer phases (pre-wet) and formulations where the powders were mixed in dry just prior to injection.

Injection of material through small lumen catheters is important for many clinical applications. Injection of material requiring only the force produced by a single hand (thought to be approximately 10 lbs±5 lbs) would enable broad usage as it would allow for tactile feedback that is relied upon in current medical practice. The injection force of a formulation of the disclosure can be tailored in some embodiments by composition and in other embodiments by the preparation method. FIG. 11 shows injection force data gathered from the injection test method (described above) versus viscosity as measured using low frequency oscillatory rheology comparing formulations where the powders were compounded into the polymer phases (AMP-1 and AMP-2) and formulations where the powders were mixed in dry just prior to injection (AMP-15, AMP-16, AMP-17, AMP-18, AMP-19, AND AMP-20). FIG. 11 demonstrates that mixing dry powders into the polymers at the time of injection results in a material that has a similar viscosity with less silica and about half the injection force (AMP-18 vs. AMP-1). Without being bound by any theory, it is thought that the polymer adsorption onto the silica surface in AMP-1 reduces the particle-to-particle interactions and silica's ability to form a network structure (requiring more silica to reach a similar viscosity) whereas when the particles are mixed at the time of injection there is less time for particle wetting and polymer adsorption resulting in a network structure with fewer particles. In addition, a reduction in polymer molecular weight further decreases the required injection force as evidenced by comparing AMP-19 and AMP-15 which have the same percentage of silica and similar viscosity but an approximate 4× decrease in injection force, allowing AMP-15 to be well below the injection force target through an 0.021" lumen catheter.

Injection test method: Injection test method: Injection was done using a 1 ml syringe at a constant rate of 0.5 ml/min. through a length of 100 cm of a 0.021" catheter.

Example 14. Impact of Silica Hydrophobicity on Stability of Preformulation Compositions The impact of silica type (hydrophobic vs. hydrophilic) on the stability of preformulation compositions of the disclosure was analyzed.

Figure 12:
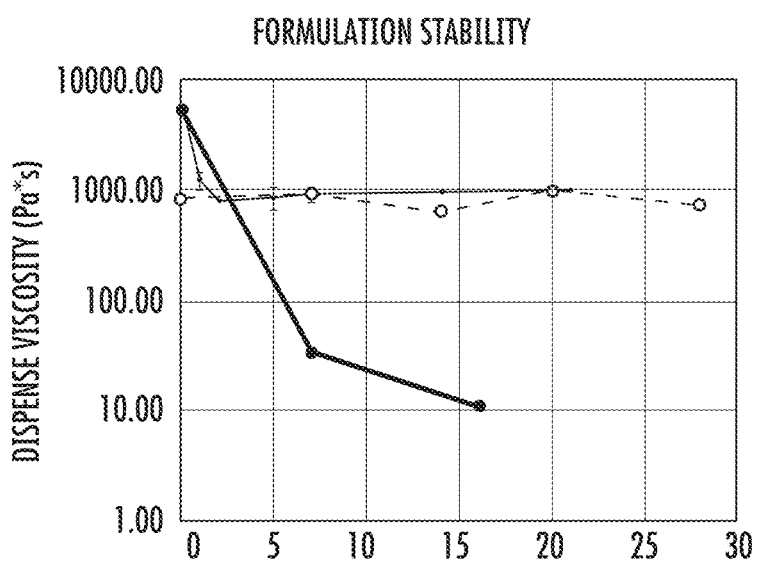
FIG. 12 shows the impact of silica type (hydrophobic vs. hydrophilic) on the stability of preformulation compositions of the disclosure.

A viscosity decrease is known to occur when hydroxyl groups present on the silica surface interact with siloxane groups present in the silicone polymer backbone. Formulations prepared with either hydrophilic (AMP-1) or hydrophobic (AMP-2) silica were prepared by compounding each phase and storing at 70° C. The rheological properties were measured under oscillation (as described above) at discrete timepoints at which point the phases were mixed. Formulations prepared with hydrophilic silica show a decrease in the measured viscosity over time, while formulations prepared with hydrophobic silica show a stable viscosity over time after an initial annealing period (FIG. 12). Formulations where hydrophilic silica was mixed in immediately prior to testing (storing the fluid silicone and silica powders separately (AMP-18)) also showed stable viscosity over time. This demonstrates that stable formulations can be prepared using hydrophobic silica, or by combining hydrophilic silica into the formulation at the time of use therefore minimizing the interaction of the silica surface with the polymer backbone.

Example 15. Impact of Hydrophilic Plasticizer on Coalescence and Ductility

Figure 13A:
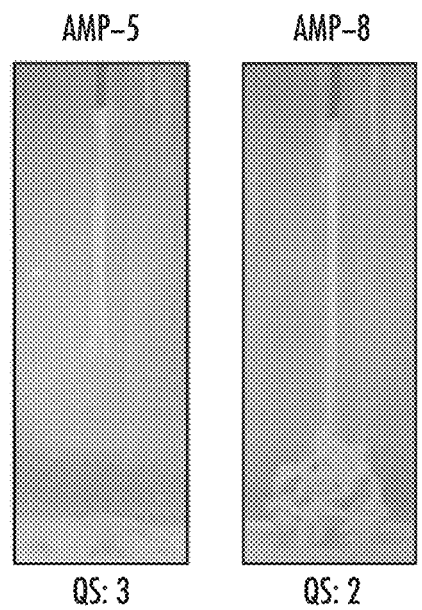
FIG. 13A shows the effect of inclusion of a hydrophilic plasticizer on coalescence of compositions of the disclosure.
Figure 13B:
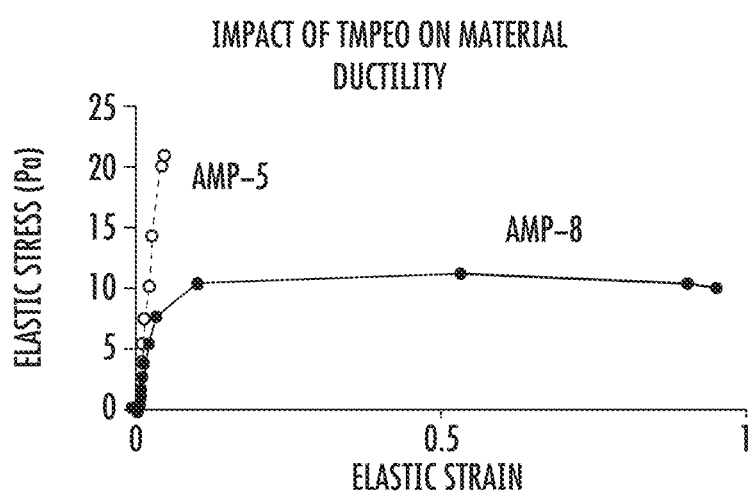
FIG. 13B shows the effect of a hydrophilic plasticizer on ductility and elasticity of the compositions.

The use of hydrophilic plasticizers has been shown to impact both the ductility/elasticity of the formulations, while also affecting the coalescence. Formulations were prepared in which bismuth trioxide was combined with the fluid phases, while fumed silica was stored separately dry and combined with the fluid phases immediately prior to testing. In one instance, trimethylolpropane ethoxylate (TMPEO) was included as a hydrophilic plasticizer (AMP-8), while in another formulation this component was missing (AMP-5). The formulations were evaluated rheologically as described above and characterized using the injection test. The results are shown in FIG. 13A. AMP-5 shows elongated droplets with good coalescence (QS score of 3), whereas AMP-8 show increased structure, with material being extruded from the catheter as a continuous stream, which then builds as a coil upon itself in the bottom of the cup as discrete volumes (QS score of 2). When measured rheologically, AMP-5 shows brittle behavior on the stress/strain curve, while the addition of TMPEO in AMP-8 improves the ductility/elasticity of the formulation (FIG. 13B).

Example 16. Impact of Level of Silica on Coalescence and Ductility

Figure 14:
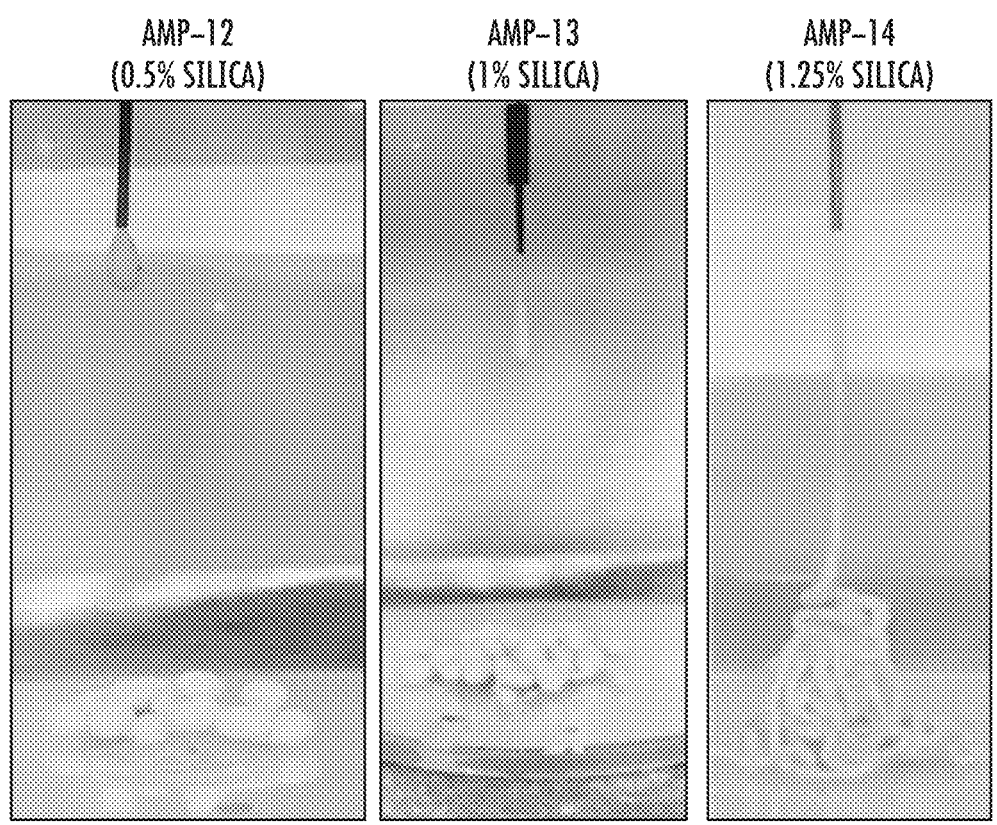
FIG. 14 shows the impact of the amount of silica on coalescence and ductility of the composition.

The level of silica used in compositions of the disclosure was found to have an impact on the physical properties of the material as injected through a catheter and characterized using the injection test. As shown in FIG. 14, the amount of silica in a system where the powders were stored dry and mixed into the polymers prior to injection impacts the ability of the formulation to build structure. Increasing silica leads to an increase in material structure due to percolation (the percolation threshold is a mathematical concept in percolation theory that describes the formation of long-range connectivity in random systems). The injection behavior can be modified from a short droplet (AMP-12), to an elongated droplet (AMP-13), to a continuous coil (AMP-14) with small increases in silica content. These different properties may each be particularly suited for a wide range of potential clinical applications depending on the desired performance.

Figure 15:
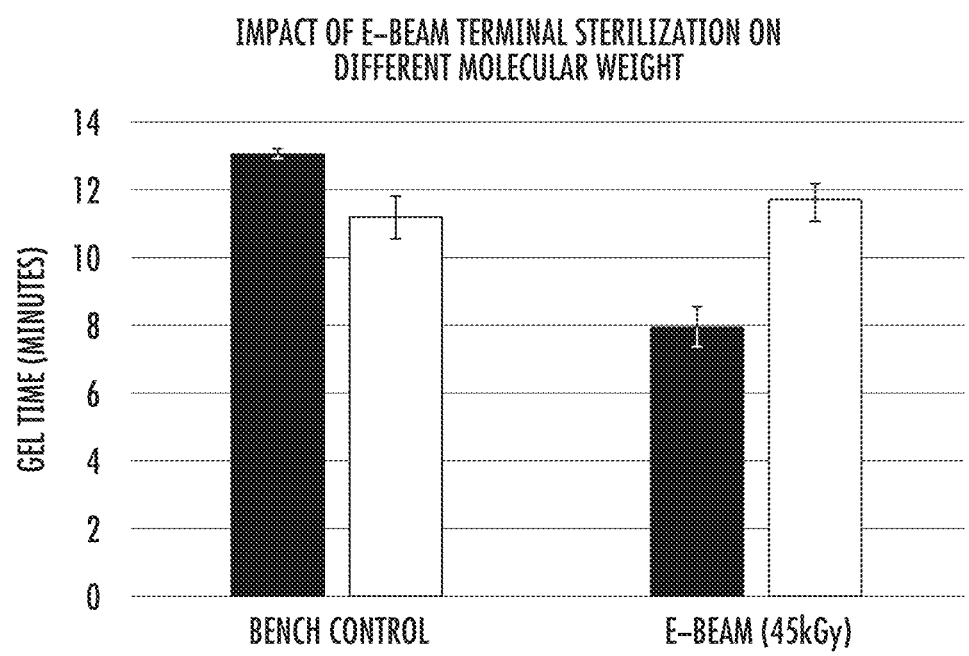
FIG. 15 shows the impact of molecular weight of the silicone components in the compositions on the ability to terminally sterilize the cross-linked compositions by electron beam sterilization.

Example 17. Impact of MW of Silicone Components on Ability to Terminally Sterilize Compositions Via Electron Beam Sterilization The molecular weight of silicone (polydimethyl siloxane, PDMS) components used in compositions of the disclosure was found to affect the ability to use terminal sterilization (electron beam, e-beam) as a modality. Two formulations were prepared with dry powders and mixed just prior to injection using two different molecular weight (MW) range PDMS components. AMP-4 comprises PDMS components of 5000-10000 Da, and AMP-3 comprises 17DMS components of 500-2000 Da. Formulations were submitted for e-beam sterilization, receiving a total dose of 45 kGy as 3, 15 kGy passes. Bench controls, receiving no e-beam sterilization were prepared for comparison. The rheological properties of the materials were evaluated. AMP-4 showed a decrease in the gel time post e-beam treatment when compared to a non-sterilized control sample. AMP-3 showed no difference in gel time post e-beam treatment when compared to a non-sterilized control sample (FIG. 15). These results demonstrate that the use of PDMS components with lower MW may enable the use of radiation based terminal sterilization modalities.

Figures 16A, 16B:
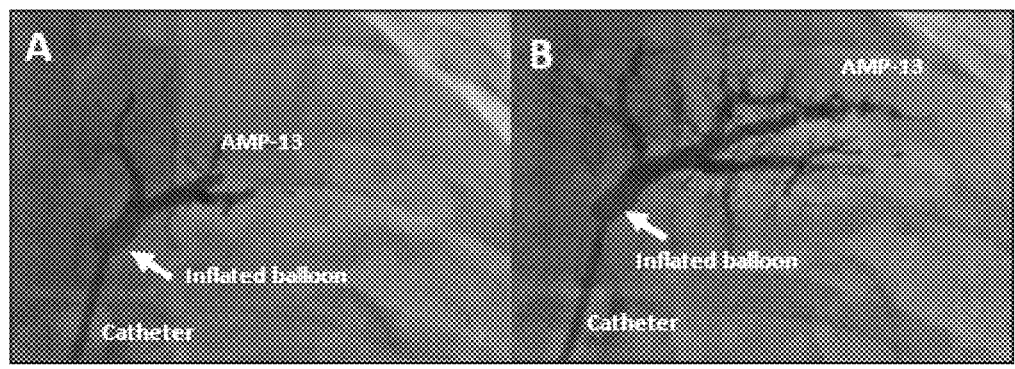
FIG. 16 A-16D shows the progressive embolization of a portion of swine vasculature during an embolization procedure with a crosslinkable composition in accordance with the present disclosure.
Figures 16C, 16D:
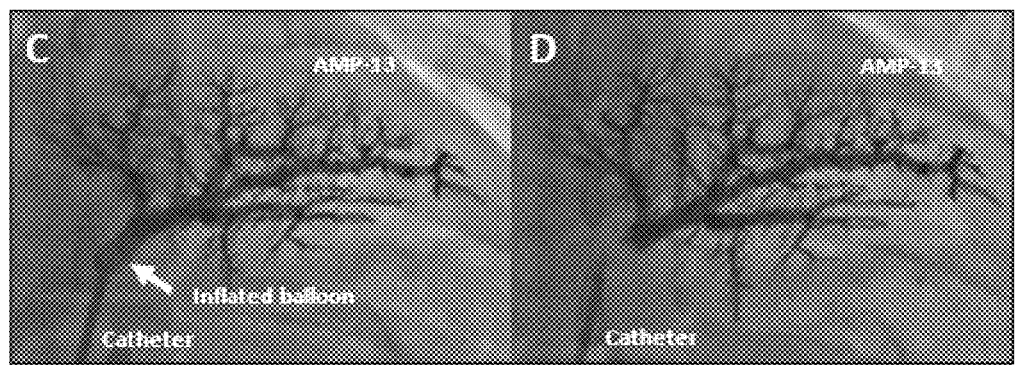

Example 18. Progressive Vascular Embolization with a Composition of the Disclosure A 4 Fr balloon catheter (9 mm diameter balloon) was used to occlude a branch of a swine portal vein. AMP-13 was prepared by mixing the dry components and fluid components just prior to injection. FIG. 16 (A-D) show the progression of the injection as taken via fluoroscopy, where (A) is the initial injection and (D) is post material cure when the occlusion balloon is deflated. AMP-13 flowed proximal to distal and was able to be injected into the very distal branches of the vessel creating a complete cast of the portal vein branch. Without being bound by theory, the shear-thinning and flow responsiveness of AMP-13 enabled this deep penetration without over pressurizing the vessel or causing the balloon to be kicked back proximally. FIG. 16D shows how, once cured, the balloon was able to be easily deflated and removed without adhesion to the material.

What is claimed is:

1. A kit for forming crosslinkable compositions for vascular embolization, said kit comprising:
   (a) a first fluid composition comprising a first polysiloxane having two or more unsaturated groups and a first imaging agent,
   (b) a second fluid composition that comprises a first hydride material having two or more hydride groups and a second imaging agent which is the same or different from the first imaging agent,
   (c) a dry composition comprising a first silica filler and optionally a second silica filler which is the same or different from the first silica filler, and
   wherein the first fluid composition, second fluid composition, and dry composition are stable, and when mixed, form a crosslinkable composition having the first and second imaging agents substantially evenly dispersed in the crosslinkable composition; and
   wherein the crosslinkable composition cures into a solid when injected into a target vessel and occludes the target vessel.

2. The kit of claim 1, further comprising one or more components for mixing the first fluid composition, the second fluid composition, and the dry composition to form a crosslinkable composition and for delivering the crosslinkable composition to a target site within a body.

3. The kit of claim 2, wherein the component for delivering the crosslinkable composition is a catheter.

4. The kit of claim 1, wherein the dry composition is mixed into the fluid compositions at the time of use to form a composition.

5. The kit of claim 1, wherein the first and second imaging agents comprise metal oxides.

6. The kit of claim 1, wherein the first and second imaging agents comprise bismuth trioxide.

7. The kit of claim 1, wherein the first and second imaging agent are of a size ranging from 10 nm to 20 μm.

8. The kit of claim 1, wherein once formed, the crosslinkable composition is injectable by hand.

9. The kit of claim 1, wherein the first silica filler and the second silica filler, if present, is hydrophobic.

10. The kit of claim 1, wherein the first and the second silica filler, if present, are the same.

11. The kit of claim 9, wherein the first and the second silica filler, if present, are fumed silica.

12. The kit of claim 1, wherein at least one of the first and second fluid compositions comprises a catalyst for catalyzing a reaction between the unsaturated groups and the hydride groups, or the kit further comprises a third and/or fourth fluid composition comprising a catalyst for catalyzing a reaction between the unsaturated groups and the hydride groups.

13. The kit of claim 12, wherein the first fluid composition comprises the catalyst and the second fluid composition does not comprise a catalyst.

14. The kit of claim 13, wherein the second fluid composition comprises a second polysiloxane having two or more unsaturated groups, and wherein the second polysiloxane is the same as or different from the first polysiloxane.

15. The kit of claim 12, wherein the second fluid composition comprises the catalyst and the first fluid composition does not comprise a catalyst.

16. The kit of claim 15, wherein the first fluid composition comprises a second hydride material having two or more hydride groups, and wherein the second hydride material is the same as or different from the first hydride material.

17. The kit of claim 1, wherein the crosslinkable composition comprises a total amount of at least 10 wt % of the first and second imaging agent.

18. The kit of claim 1, wherein the ratio of the volume of the first fluid composition to the volume of the second fluid composition is in the range of from 4:1 to 1:4.

19. The kit of claim 1, wherein the crosslinkable composition comprises a molar ratio of vinyl groups to hydride groups of ≥0.9:1.

20. The kit of claim 1, wherein the first polysiloxane is a vinyl-terminated polysiloxane, an acrylate-terminated polysiloxane, or a methylacrylate-terminated polysiloxane.

21. The kit of claim 1, wherein the first polysiloxane has a weight average molecular weight ranging from 250 Da to 10,000 Da.

22. The kit of claim 1, wherein the first polysiloxane is a multifunctional polysiloxane hydride having a weight average molecular weight ranging from 300 to 13,000 Da.

23. The kit of claim 1, wherein the crosslinkable composition contains a catalyst modifier.

24. The kit of claim 1, wherein the first fluid composition, second fluid composition, dry composition and/or the crosslinkable composition are subjected to terminal sterilization.

25. A method comprising
(a) forming a crosslinkable composition for vascular embolization comprising:
annealing a first fluid composition comprising a first polysiloxane having two or more unsaturated groups and a first imaging agent, annealing a second fluid composition comprising a hydride material having two or more hydride groups and a second imaging agent that is the same or different from the first imaging agent, and at the time of use, mixing the first and second fluid compositions with a dry composition comprising a first silica filler and optionally a second silica filler that is the same or different from the first silica filler to form the crosslinkable composition, wherein the first and second imaging agents are substantially evenly dispersed in the crosslinkable composition and
(b) injecting the crosslinkable composition into the vasculature of a patient whereupon the crosslinkable composition crosslinks and forms a solid which occludes a target vessel into which it is injected.

26. The method of claim 25 wherein the method is a vascular embolization method.

27. The method of claim 25, wherein method is a method for (1) occlusion of the vasculature for treatment of tumors, (2) pre-surgical embolization of tumors, (3) treatment of chronic subdural hematoma, brain aneurysms, arteriovenous malformations, arteriovenous fistulas, gastrointestinal bleeds, bleeding due to trauma, abdominal aortic aneurysm, intracranial aneurysm, pulmonary aneurysm, or hemorrhage, (4) prostate artery embolization or uterine artery embolization, (5) treatment of visceral aneurysms, varicoceles, or varices, (6) treatment for pelvic congestion, (7) treatment of epistaxis or (8) treatment of endoleaks.

28. The method of claim 25, wherein the method further comprises identifying a blood vessel that branches into smaller distal vessels and injecting the crosslinkable composition into the blood vessel such that the crosslinkable composition flows into the distal vessels and occludes the distal vessels.

29. The method of claim 25, wherein the crosslinkable composition is injected into the vasculature or neurovasculature of the patient via a catheter.

* * * * *